(12) United States Patent
Greenberg et al.

(10) Patent No.: US 9,545,422 B2
(45) Date of Patent: Jan. 17, 2017

(54) METHODS OF INDUCING PHOTOSENSITIVITY BY TARGETING CHANNELRHODOPSIN-2 AND HALORHODOPSIN TO SUBCELLULAR REGIONS OF RETINAL GANGLION CELLS

(75) Inventors: Kenneth P. Greenberg, Oakland, CA (US); Frank Werblin, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 1089 days.

(21) Appl. No.: 13/027,109

(22) Filed: Feb. 14, 2011

(65) Prior Publication Data

US 2011/0224145 A1 Sep. 15, 2011

Related U.S. Application Data

(60) Provisional application No. 61/309,228, filed on Mar. 1, 2010.

(51) Int. Cl.
| | | |
|---|---|---|
| *A61K 38/00* | (2006.01) | |
| *A61K 39/00* | (2006.01) | |
| *A61B 5/00* | (2006.01) | |
| *C12N 15/00* | (2006.01) | |
| *C12N 15/11* | (2006.01) | |
| *C12N 15/113* | (2010.01) | |
| *C07K 14/00* | (2006.01) | |
| *A61K 31/713* | (2006.01) | |
| *A61K 38/17* | (2006.01) | |
| *A61K 45/06* | (2006.01) | |
| *C12N 5/079* | (2010.01) | |

(52) U.S. Cl.
CPC ........... *A61K 31/713* (2013.01); *A61K 38/177* (2013.01); *A61K 38/1796* (2013.01); *A61K 45/06* (2013.01); *C12N 5/0621* (2013.01)

(58) Field of Classification Search
CPC .. A61K 2300/00; A61K 38/177; A61K 45/06; A61K 48/005; A61K 35/30; A61N 1/36046; A61N 5/062; A61N 5/0622; C07K 14/4702; C07K 2319/01; C07K 14/705; C12N 15/8616; C12N 2750/14143; C12N 5/0621; G01N 2800/52; G01N 33/6872; C12Q 2600/158
See application file for complete search history.

(56) References Cited

U.S. PATENT DOCUMENTS

| | | | |
|---|---|---|---|
| 4,861,719 A | 8/1989 | Miller | |
| 5,139,941 A | 8/1992 | Muzyczka et al. | |
| 5,356,806 A | 10/1994 | Harris et al. | |
| 5,948,902 A | 9/1999 | Honkanen et al. | |
| 2007/0053996 A1* | 3/2007 | Boyden et al. | 424/718 |
| 2007/0054319 A1* | 3/2007 | Boyden et al. | 435/7.1 |
| 2007/0261127 A1* | 11/2007 | Boyden et al. | 800/18 |
| 2010/0234273 A1* | 9/2010 | Boyden et al. | 514/3 |
| 2010/0262212 A1* | 10/2010 | Shoham et al. | 607/88 |
| 2011/0125077 A1* | 5/2011 | Denison et al. | 604/20 |
| 2011/0125078 A1* | 5/2011 | Denison et al. | 604/20 |
| 2012/0093772 A1* | 4/2012 | Horsager et al. | 424/93.2 |
| 2012/0258530 A1* | 10/2012 | Balya et al. | 435/325 |

OTHER PUBLICATIONS

Lagali et al. Nat. Neurosci. 2008, 11: 667-674.*
Retinal ganglion On-and Off-center cells retrieved from website www.cns.nyu.edu/~david/courses/perception/lecturenotes/ganglion/ganglion.html, on Mar. 10, 2014.*
Elias et al. Trends in Cell Biol. 2007, 17: 344-352.*
Ayalon et al. (2008) "An ankyrin-based mechanism for functional organization of dystrophin and dystroglycan" Cell 135(7):1189-1200.
Craven & Bredt (2000) "Synaptic targeting of the postsynaptic density protein PSD-95 mediated by a tyrosine-based trafficking signal" J. Biol. Chem. 275(26):20045-20051.
Dacey (1993) "The mosaic of midget ganglion cells in the human retina" J Neurosci 13(12):5334-5355.
Degenaar et al. (2009) "Optobionic vision—a new genetically enhanced light on retinal prosthesis" J Neural Eng 6(3):035007.
Elango et al. (1988) "Molecular cloning and characterization of six genes, determination of gene order and intergenic sequences and leader sequence of mumps virus" J. Gen. Virol. 69(Pt. 11):2893-2900.
El-Husseini et al. (2000) "Dual palmitoylation of PSD-95 mediates its vesiculotubular sorting, postsynaptic targeting, and ion channel clustering" J. Cell Biol.148(1):159-172.
Giesemann et al. (2003) "Complex formation between the postsynaptic scaffolding protein gephyrin, profilin, and Mena: a possible link to the microfilament system" J. Neurosci. 23(23):8330-8339.
Goldin (1999) "Diversity of mammalian voltage-gated sodium channels" Annals N.Y. Academy of Sciences 868:38-50.
Gradinaru et al. (2008) "eNpHR: a Natronomonas halorhodopsin enhanced for optogenetic applications" Brain Cell Biol. 36(1-4):129-139.
Greenberg et al. (2007) "Targeted transgene expression in müller glia of normal and diseased retinas using lentiviral vectors" Invest Ophthalmol. Vis Sci 48(4):1844-1852.
Han & Boyden (2007) "Multiple-color optical activation, silencing, and desynchronization of neural activity, with single-spike temporal resolution" PLoS One 2(3):e299.
Huberman et al. (2009) "Genetic identification of an On-Off direction-selective retinal ganglion cell subtype reveals a layer-specific subcortical map of posterior motion" Neuron 62(3):327-334.
Koizumi et al. (2007) "Organotypic culture of physiologically functional adult mammalian retinas" PLoS One 2(2):e221.
Kordeli et al. (1995) "AnkyrinG. A new ankyrin gene with neural-specific isoforms localized at the axonal initial segment and node of Ranvier" J Biol Chem 270(5):2352-2359.
Mazzoni et al (2008) "Retinal ganglion cells survive and maintain normal dendritic morphology in a mouse model of inherited photoreceptor degeneration" J Neurosci 28(52):14282-14292.

(Continued)

*Primary Examiner* — Chang-Yu Wang
(74) *Attorney, Agent, or Firm* — Edward J. Baba; Shweta Chandra; Bozicevic, Field & Francis LLP

(57) ABSTRACT

The present disclosure provides neuromodulators, nucleic acid encoding thereof, and compositions thereof for endowing visual processing abilities to neuronal cells. The present disclosure further provides a method of restoring light sensitivity to degenerate retinas.

8 Claims, 10 Drawing Sheets

(56) References Cited

OTHER PUBLICATIONS

Takeuchi et al. (1993) "In vitro transcription and replication of the mumps virus genome" Archiv. Virol., 128(1-2):177-183.
Tanabayashi et al. (1993) "Identification of an amino acid that defines the fusogenicity of mumps virus" J. Virol. 67(5):2928-2931.
Topinka & Brendt (1998) "N-terminal palmitoylation of PSD-95 regulates association with cell membranes and interaction with K+ channel Kv1.4" Neuron 20(1):125-134.
Zhang & Bennett (1998) "Restriction of 480/270-kD ankyrinG to axon proximal segments requires multiple ankyrinG-specific domains" J Cell Biol 142(6):1571-1581.
Bean (1989) "Classes of calcium channels in vertebrate cells" Ann. Rev. Physiol. 51:367-384.
Bennett et al. (1993) "The spectrin-based membrane skeleton and micron scale organization of the plasma membrane" Annu Rev Cell Biol 9:27-66.
Greger (1988) "Chloride transport in thick ascending limb, distal convolution, and collecting duct" Annu. Rev. Physiol. 50:111-122.
Hess (1990) "Calcium channels in vertebrate cells" Ann. Rev. Neurosci. 13:337-356.
Kaplan et al. (1997) "Induction of sodium channel clustering by oligodendrocytes" Nature 386(6626):724-728.
Kawano et al. (1990) "Complete nucleotide sequence of the matrix gene of human parainfluenza type 2 virus and expression of the M protein in bacteria" Virol. 179(2):857-861.
Lee et al. (1998) "Receptive fields of primate retinal ganglion cells studied with a novel technique" Vis Neurosci 15(1):161-175.
Rosenfeld et al. (1991) "Adenovirus-mediated transfer of a recombinant alpha 1-antitrypsin gene to the lung epithelium in vivo" Science 252(5004):431-434.
Rosenfeld et al. (1992) "In vivo transfer of the human cystic fibrosis transmembrane conductance regulator gene to the airway epithelium" Cell 68(1):143-155.
Scheraga (1992) "Predicting Three-Dimensional Structures of Oligopeptides" Rev. Computational Chem. 3:73-142.
Srinivasan et al. (1988) "Ankyrin and spectrin associate with voltage-dependent sodium channels in brain" Nature 333(6169):177-180.
Swandlilla et al. (1991) "Do calcium channel classifications account for neuronal calcium channel diversity?" Trends in Neuroscience 14(2)146-51.
Tanabayashi et al. (1992) "Expression of mumps virus glycoproteins in mammalian cells from cloned cDNAs: both F and HN proteins are required for cell fusion" Virol. 187(2):801-804.
Vacher et al., "Localization and Targeting of Voltage-Dependent Ion Channels in Mammalian Central Neurons," Physiol. Rev. 88:1407-1447 (2008).
Yau and Hardie, "Phototransduction Motifs and Variations," Cell 139:246-264 (2009).
Chambers, et al. "Light-Induced Depolarization of Neurons Using a Modified Shaker K+ Channel and a Molecular Photoswitch", J Neurophysiol, 96:2792-2796, 2006.
Chow, et al. "High-Performance Genetically Targetable Optical Neural Silencing via Light-Driven Proton Pumps", Nature. Jan. 7, 2010; 463(7277): 98-102.
Koizumi, et al. "Organotypic Culture of Physiologically Functional Adult Mammalian Retinas", PLoS One, Issue 2, e221, pp. 1-8, 2007.
Lim, et al."A Novel Targeting Signal for Proximal Clustering of the Kv2.1 K1 Channel in Hippocampal Neurons", Neuron, Vol, 25, 385-397, Feb. 2000.
Volgraf, et al. "Allosteric control of an ionotropic glutamate receptor with an optical switch", Nat Chem Biol. Jan. 2006 ;2(1): 47-52.

* cited by examiner

SEQUENCE LISTING

```
<160> NUMBER OF SEQ ID NOS: 8

<210> SEQ ID NO 1
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 1

Gly Ser Gly Gly Ser
 1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 2

Gly Gly Gly Ser
 1

<210> SEQ ID NO 3
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 3

Gly Gly Ser Gly
 1

<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 4

Gly Gly Ser Gly Gly
 1               5

<210> SEQ ID NO 5
<211> LENGTH: 5
<212> TYPE: PRT
<213> ORGANISM: Artificial Sequence
```

```
<220> FEATURE:
<223> OTHER INFORMATION: Synthetic polypeptide

<400> SEQUENCE: 5

Gly Ser Gly Ser Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 6

Gly Ser Gly Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 7

Gly Gly Gly Ser Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 8

Gly Ser Ser Ser Gly
1               5
```

METHODS OF INDUCING PHOTOSENSITIVITY BY TARGETING CHANNELRHODOPSIN-2 AND HALORHODOPSIN TO SUBCELLULAR REGIONS OF RETINAL GANGLION CELLS

CROSS-REFERENCE TO RELATED APPLICATION

Pursuant to 35 U.S.C. §119(e), this application claims priority to the filing date of U.S. Provisional Patent Application Ser. No. 61/309,228, filed Mar. 1, 2010, which application is incorporated herein by reference in its entirety.

STATEMENT REGARDING FEDERALLY SPONSORED RESEARCH

This invention was made with government support under grant numbers 5R01EY015512-06 and F32EY018790-01 awarded by the National Institute of Health. The government has certain rights in the invention.

INTRODUCTION

Center-surround antagonism is found in nearly every sensory system and is a fundamental aspect of visual information processing. Recordings of vertebrate cone photoreceptor light responses demonstrated that illumination of the surround counter-acts illumination of the center. In the vertebrate retina, bipolar cells are the recipients of these photoreceptor signals and have center-surround antagonistic receptive fields, which they transmit to ganglion cells. These lateral interactions are present throughout the inner and outer plexiform layers and lead to robust center-surround opponency found in almost all ganglion cell types. Center-surround antagonism allows for fundamental visual information processing including local gain control and edge detection in the retina, and motion segmentation as well as in shape-from-motion processing in the visual cortex. In a degenerate retina, the ability for visual information processing is lost due to the loss of photoreceptors and the remodeling and differentiation of the inner retina. There remains a need to for compositions and methods that allow for restoration of light sensitivity to a degenerate retina.

SUMMARY OF THE INVENTION

The present disclosure provides neuromodulators and methods of use to enable neuronal cells to process visual information. In one embodiment, the optical neuromodulators channelrhodopsin-2 (hChR2) and halorhodopsin (eNpHR) were selectively targeted differentially into the soma and/or dendrites of ganglion cells to reestablish antagonistic center-surround receptive field interactions. This establishes an antagonistic relationship between dendrites and soma. Therefore, the functional dimensions of these interactions are expanded by convolving the native response areas of soma and dendrites with Gaussian-filtered versions of the visual scene. The convolutions approximate receptive field interactions of parafoveal ganglion cells and enable proper edge extraction. This approach bypasses the more distal areas of retinal degeneration and can restore sight to individuals suffering from retinal disease.

DEFINITIONS

Figure 1:
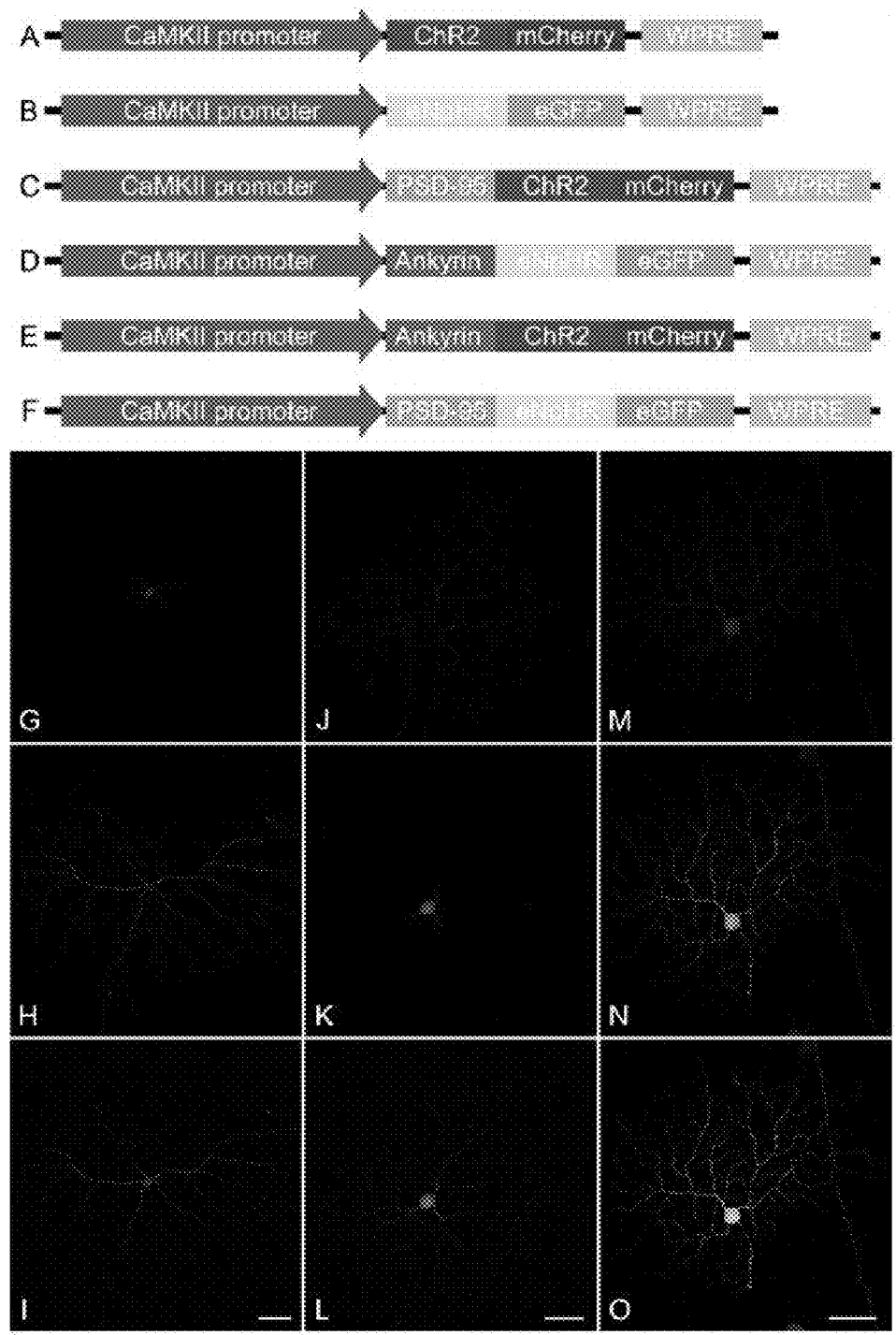
FIG. 1. hChR2 and eNpHR constructs and transgene expression in whole mount rabbit retina. The calcium/calmodulin-dependent protein kinase II (CaMKIIa) promoter and woodchuck hepatitis virus post-transcriptional regulatory element (WPRE) to drive high transgene expression levels in ganglion cells were used in all constructs. (A) Plasmid map of untargeted hChR2-mCherry fusion. (B) Untargeted eNpHR-eGFP fusion. (C) Post-synaptic density 95 (PSD-95) targeting motif fused with hChR2-mCherry for dendritic localization. (D) Ankyrin$_G$ motif fused with eNpHR-eGFP for somatic localization. (E) Ankyrin$_G$ motif fused with hChR2-mCherry. (F) PSD-95 fused with eNpHR-eGFP. (G) Confocal image of rabbit ganglion cell expressing Ankyrin$_G$-hChR2-mCherry localized to the soma and proximal dendrites (red). (H) Same cells as G showing PSD95-eNpHR-eGFP localized to the dendrites (green). (I) Merge of G & H. Scale bar represents 100 µm. (J) PSD95-hChR2-mCherry localized to the dendrites. (K) Ankyrin$_G$-eNpHR-eGFP localized to the soma and proximal dendrites. (L) Merge of J & K. Scale bar represents 100 µm. (M) Untargeted hChR2-mCherry is localized throughout the plasma membrane. (N) Untargeted eNpHR-eGFP is localized throughout the plasma membrane. (O) Merge of M & N. Scale bar represents 100 µm.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The following terms have the following meanings unless otherwise indicated. Any undefined terms have their art recognized meanings.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained.

The term "pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

"Derived from" in the context of an amino acid sequence or polynucleotide sequence (e.g., an amino acid sequence "derived from" PSD-95) is meant to indicate that the polypeptide or nucleic acid has a sequence that is based on that of a reference polypeptide or nucleic acid (e.g., a naturally occurring PSD-95 protein or encoding nucleic acid), and is not meant to be limiting as to the source or method in which the protein or nucleic acid is made.

As used herein, "neuromodulators" are agents such as neurotransmitters or receptors (e.g. 7-membrane spanning G-protein coupled receptors), whose presence or activity can influence and/or modulate the overall long-term activity of neurons and their connectivity.

Modulators (e.g. neuromodulators) of use in the present disclosure include members of the opsin gene family such as, for example, melanop sin, vaopsin, pinopsin, parapinopsin, rod opsin, cone opsins, TMT opsin, neuropsin (OPN5), and opsins from photoreceptive structures of invertebrate species.

Opsins are light-activated G protein-coupled receptors that are found in photosensitive cells of vertebrates and invertebrates. Opsins are typically seven transmembrane receptors and are typically associated with a chromophore to form a photosensitive substance. "Opsins", as used herein, include all G protein-coupled receptors that share at least 20% deduced amino acid similarity with bovine rod opsin (accession no. P02699). Members of the opsin family include vaopsin, pinopsin, parapinopsin, rod opsin, cone opsins, TMT opsin, neuropsin (OPN5), and opsins from photoreceptive structures of invertebrate species and non-mammalian vertebrate species (such as lamprey parapinopsin; accession no. Q98980).

The term "retinal ganglion cells" is a generic term which includes all of the output neurons of the retina, the vast majority of which (for example 99%) project to the visual areas of the brain. In classical physiology these include 'ON' and 'OFF' center cells that are respectively excited or inhibited by light presented at the receptive filed centre.

By "in response to light" we include a response to light stimuli in the cone (photopic) brightness range and to the presentation of electromagnetic radiation of wavelength within the range of about 300 to about 900 nm, for example.

By "inducing photosensitivity" we include inducing the ability of a cell (or cells) that is not sensitive to light or that has a relatively low sensitivity to light, to detect and/or respond to light.

For example, photosensitivity may be induced by introducing and expressing gene(s) encoding component(s)

involved in a photo-transduction cascade into a cell, or by inducing the expression of gene(s) encoding component(s) involved in a photo-transduction cascade which are usually present in the genome of a cell but which are not usually expressed (for example, due to transcriptional or translational silencing of the gene).

Measuring and/or determining an increase in photosensitivity can include measuring the depolarisation of transformed cells in culture and/or by examining the behavioural and/or physiological responses of a whole organism in which the cell (or cells) of interest are present. Such methods are well known to those skilled in the arts of, for example, molecular biology, neurobiology and/or zoology. Cellular depolarisation may be measured electro-physiologically using single electrodes or by imaging cells or tissue slices in culture, using a combination of potentiometric and calcium dyes. In the case of chronic stimulation assays measuring and/or determining c-FOS expression or cell death may be used.

By "effective amount", it is meant to include an amount that is sufficient to induce photosensitivity, edge detection, and/or center surround antagonism, in one or more neuronal cells and thereby restore sight and/or alleviate blindness in an individual. An effective amount may be determined by use of the methods described in the Example section for measuring and/or detecting whether sight has been restored and/or blindness has been alleviated. Alternatively, an idea of the effective range of a medicament may be obtained by testing the medicament on neuronal cells in vitro.

As used herein, "center surround antagonism", refers to antagonistic interactions between center and surround regions of the receptive fields of photosensitive cells in the retina. Center surround antagonism enables edge detection and contrast enhancement within the visual cortex.

It must be noted that as used herein and in the appended claims, the singular forms "a," "an," and "the" include plural referents unless the context clearly dictates otherwise. Thus, for example, reference to "a neuromodulator of protein function" includes a plurality of such regulators and reference to "the ligand" includes reference to one or more ligands and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides a photoreactive neuromodulator of protein function. The present disclosure further provides a light-regulated polypeptide that includes a subject neuromodulator. Also provided are cells and membranes comprising a subject light-regulated polypeptide. The present disclosure further provides methods of modulating protein function, involving use of light.

Overview

The present disclosure provides a method to restore center-surround antagonism directly to ganglion cells in a retina lacking photoreceptor input. Characterizations of how visual information would be encoded by arrays of these engineered neurons are also provided.

The insertion of optical neuromodulators into normally non-photosensitive retinal neurons is a promising approach for restoring sight to profoundly blind individuals. Methods can involve delivery of channels, such as the directly photosensitive cation channel channelrhodopsin-2 (ChR2), synthetically engineered potassium (SPARK) and glutamate (LiGluR) channels, and the G-protein coupled receptor melanopsin, to normally non-photosensitive bipolar, amacrine, and ganglion cells. The subject methods can restore light sensitivity to a degenerate retina, provide prosthetic interventions to transmit light-driven information to higher visual centers, and prove to improve visually-guided behaviors.

The subject methods have the benefits of retaining crucial retinal information processing capability while being independent of the state of inner retinal circuit remodeling during degeneration. In accordance with the subject methods, an excitatory center and a truly antagonistic surround are genetically reconstructed directly at the ganglion cell membrane by targeting antagonistic opsins to discrete subcellular domains. The visual image is then preprocessed with differential Gaussian blurring at each wavelength to approximate the relative dimensions of the antagonistic receptive field center and surround. Direct measurement and simulation can demonstrate that dynamic control of edge extraction can be attained by spatio-chromatic image preprocessing of excitatory and inhibitory input channels.

Methods

The present disclosure provides methods to restore sight. The method can restore photosensitivity, center surround antagonism, and/or edge detection to a retina without little or no functional photoreceptors. The method involves administering a first neuromodulator and a second neuromodulator to be expressed in a retinal neuronal cell (e.g. bipolar or ganglion cell), in which the first neuromodulator causes a synaptic potential that increases the chance that a future action potential will occur and the second modulator causes a synpatic potential that decreases the chance that a future action potential will occur. In the subject method, the first neuromodulator is directed to be expressed at a subcellular location different from the second neuromodulator.

The first and second neuromodulators can be ion channels that have opposite potentiating function, such that if the first neuromodulator is excitatory the second neuromodulator is inhibitory and vice versa. Where the first neuromodulator is an excitatory channel, the first neuromodulator allows the flow of positively-charged ions into the neuron, which in turn can depolarize the membrane potential of the cell. Where the second neuromodulaor is an inhibitory channel, it pumps negatively-charge ions into the neuron and/or allows the flow of the positively-charged ions out of the neuron. An inhibitory channel can then polarize and/or hyperpolarize the membrane.

Neuromodulators that can be used in the subject methods encompasses ligands (e.g. neurotransmitters, such as dopamine, serotonin, acetylcholine, histamine) and receptor proteins. Examples of a neuromodulator protein include 7-membrane spanning G-protein coupled receptors. The receptors can be ligand-gated, voltage-gated, and/or light-sensitive (e.g. opsins). Receptors that can be administered as neuromodulators to be expressed in targeted locales include sodium channels, potassium channels, calcium channels, and chloride channels. Details of channels that can be used in the subject methods are provided below.

Opsins

As noted above, opsins encompass proteins that are associated with a chromophore to form a photosensitive substance. Where the opsin is prokaryotic in origin, it is a type I opsin with a seven transmembrane domain structure similar to that found in eukaryotic G-protein coupled receptors. Examples of type 1 opsins include those such as proteo-, halo- and bacteriorhodopsin.

Where the opsins are eukaryotic, the opsins can be the classical type 2 opsin groups or the novel type 2 opsin groups One example of a type 2 opsin that can be used in the subject method is rhodopsin, which is used in night vision, is a thermally stable opsin found in the rod photoreceptor cells. Cone opsins, employed in color vision, are less stable opsins located in the cone photoreceptor cells. Cone opsins are further subdivided according to their absorption maxima ($\lambda$max), the wavelength at which the highest light absorption is observed. For example, humans and other organisms have the following set of photoreceptor proteins responsible for vision:

TABLE 1

Opsin Summary

| Channel Name & Gene Symbol | Sub-type/Alternate Names | Organism source/Tissue Distribution/Notes | Accession Number |
|---|---|---|---|
| Rhodopsin | Rh1, OPN2, RHO | rod cells, used in night vision | P08100 |
| Channelrhodopsin-2 | | *Volvox carteri* f. *nagariensis* | B4Y105 |
| Channelrhodopsin-1 | | *Volvox carteri* f. *nagariensis* | B4Y103 |
| Halorhodopsin | VNG_0180G | *Halobacterium salinarium* | P16102 |
| | | *Natronomonas pharaonis* | P15647 |
| | | *Halobacterium halobium* | Q48314 |
| | | *Halobacterium halobium* | P33970 |
| | | *Halobacterium halobium* | Q48315 |
| | | *Halobacterium* sp. | O93741 |
| | | *Halorubrum sodomense* | O93742 |
| | | *Halobacterium* sp. | P33742 |
| | Sensory rhodopsin-1 | *Halobacterium salinarium* | P25964 |
| photopsins | LWS, OPN1LW | Long Wavelength Sensitive | P04000 |
| | RH2 or MWS | Middle Wavelength Sensitive | P04001 |
| | SWS1 | Short Wavelength Sensitive 1 | Q19AV6, Q96C19, Q9W6A9 |
| | SWS2, OPN1SW (BCP) | Short Wavelength Sensitive | P03999 |
| Opsin-3 | Encephalopsin; Panopsin | | Q9H1Y3 |
| Opsin-4 | Melanopsin | | Q9UHM6 |
| Opsin-5 | Neuropsin | | Q6U736 |
| RPE-retinal G protein-coupled receptor | | | P47804 |
| Photoreceptor-specific nuclear receptor | | | Q9Y5X4 |
| Cone-rod homeobox protein | CRX (CORD2) | | O43186 |
| G protein-coupled receptor kinase 7 | GRK7 (GPRK7) | | Q8WTQ7 |
| Visual system homeobox 1 | VSX1 (RINX) | | Q9NZR4 |
| Visual pigment-like receptor peropsin | RRH | | O14718 |

Light is absorbed by photosensitive substances in the rods and cones. Light absorption induces a conformational change in the structure of these substances and triggers a sequence of events that transmits a signal to the brain. As seen in the summary table above, the photosensitive substances in the rods and cones of humans and most other mammals are made up of a protein called an opsin, and retinal$_1$, the aldehyde of vitamin A$_1$. Opsin-like molecules are known in the art and have also been described in fish and other vertebrates. The photosensitive substance in rods is called rhodopsin that comprises an opsin called rodopsin, which is a G protein-coupled seven-transmembrane receptor, to which retinal$_1$ is attached. Cones possess a distinct photosensitive substance that is similar in structure to rhodopsin.

Upon exposure to light, the retinal in rhodopsin is converted from an 11-cis configuration to an all-trans isomer. This induces a confrontational change in the structure of the opsin that activates a heterotrimeric G protein called transducin or $G_\alpha$ which is associated with the intracellular domains of the classical rod and cone opsins. The G protein exchanges GDP for CTP, allowing the α-subunit to dissociate from the βγ-subunits and activate downstream effectors, such as cGMP phosphodiesterase, which result in the generation of a signal. All-trans retinal, is subsequently released from activated rhodopsin and the opsin associates with 11-cis retinal$_1$ that is produced by cells of the retinal pigment epithelium (RPE) to regenerate inactive rhodopsin.

Light-Sensitivity of Opsins

Where more than one opsins are used in the subject method, the opsins may differ in the wavelength of light that activates the opsins. The first wavelength and the second wavelength (that can activate first and second opsins respectively) can differ from one another by from about 1 nm to about 2000 nm or more, e.g., from about 1 nm to about 10 nm, from about 10 nm to about 20 nm, from about 20 nm to about 50 nm, from about 50 nm to about 75 nm, from about 75 nm to about 100 nm, from about 100 nm to about 125 nm, from about 125 nm to about 150 nm, or from about 150 nm to about 200 nm, from about 200 nm to about 500 nm, from about 500 nm to about 800 nm, from about 800 nm to about 1000 nm, from about 1000 nm to about 1500 nm, from about 1500 nm to about 2000 nm, or more than 2000 nm.

The wavelength of light that can activate an opsin ranges from $10^{-8}$ m to about 1 m, e.g., from about $10^{-8}$ m to about $10^{-7}$ m, from about $10^{-7}$ m to about $10^{-6}$ m, from about $10^{-6}$ m to about $10^{-4}$ m, from about $10^{-4}$ m to about $10^{-2}$ m, or from about $10^{-2}$ m to about 1 m. "Light," as used herein, refers to electromagnetic radiation, including, but not limited to, ultraviolet light, visible light, infrared, and microwave.

The wavelength of light that can activate an opsin in some embodiments from about 200 nm to about 800 nm, e.g., from about 200 nm to about 250 nm, from about 250 nm to about 300 nm, from about 300 nm to about 350 nm, from about 350 nm to about 400 nm, from about 400 nm to about 450 nm, from about 450 nm to about 500 nm, from about 500 nm to about 550 nm, from about 550 nm to about 600 nm, from about 600 nm to about 650 nm, from about 650 nm to about 700 nm, from about 700 nm to about 750 nm, or from about 750 nm to about 800 nm, or greater than 800 nm.

The difference between the first wavelength and the second wavelength can range from about 1 nm to about 2000 nm or more, as described above. The intensity of the light can vary from about 1 W/m$^2$ to about 50 W/m$^2$, e.g., from about 1 W/m$^2$ to about 5 W/m$^2$, from about 5 W/m$^2$ to about 10 W/m$^2$, from about 10 W/m$^2$ to about 15 W/m$^2$, from about 15 W/m$^2$ to about 20 W/m$^2$, from about 20 W/m$^2$ to about 30 W/m$^2$, from about 30 W/m$^2$ to about 40 W/m$^2$, or from about 40 W/m$^2$ to about 50 W/m$^2$. The intensity of the light can vary from about 1 μW/cm$^2$ to about 100 μW/cm$^2$, e.g., from about 1 μW/cm$^2$ to about 5 μW/cm$^2$, from about 5 μW/cm$^2$ to about 10 μW/cm$^2$, from about 10 μW/cm$^2$ to about 20 μW/cm$^2$, from about 20 μW/cm$^2$ to about 25 μW/cm$^2$, from about 25 μW/cm$^2$ to about 50 μW/cm$^2$, from about 50 μW/cm$^2$ to about 75 μW/cm$^2$, or from about 75 μW/cm$^2$ to about 100 μW/cm$^2$. In some embodiments, the intensity of light varies from about 1 μW/mm$^2$ to about 1 W/mm$^2$, e.g., from about 1 μW/mm$^2$ to about 50 μW/mm$^2$, from about 50 μW/mm$^2$ to about 100 μW/mm$^2$, from about 100 μW/mm$^2$ to about 500 μW/mm$^2$, from about 500 μW/mm$^2$ to about 1 mW/mm$^2$, from about 1 mW/mm$^2$ to about 250 mW/mm$^2$, from about 250 mW/mm$^2$ to about 500 mW/mm$^2$, or from about 500 mW/mm$^2$ to about 1 W/mm$^2$.

Sodium Channels

A variety of different isoforms of mammalian voltage dependent sodium channels have been identified, and are summarized below in Table 2. These channels can be classified into three main groups (for review see Goldin, Annals N.Y. Academy of Sciences 868:38-50, 1999).

TABLE 2

Sodium Channel Sub-type Summary

| Channel Name & Gene Symbol | Sub-type/ Alternate names | Tissue Distribution | Accession Number |
| --- | --- | --- | --- |
| SCN1A (Nav1.1) | Rat I (rat) | CNS/PNS | X03638 |
|  | HBSCI (human) | CNS | X65362 |
|  | GPB1 (guinea pig) | CNS | AF003372 |
| SCN2A (Nav1.2) | Rat (rat) | CNS | X03639 |
|  | HBSCH (human) | CNS | X65361 |
|  | HBA (human) | CNS | M94055 |
| Nav 1.2A | Rat IIA | CNS | X61149 |
| SCN3A(Nav 1.3) | Rat III (rat) | CNS | Y00766 |
| SCN4A (Nav1.4) | SkM1, μ1 (rat) | Skeletal muscle | M26643 |
|  | SkM1 (human) | Skeletal muscle | N81758 |
| SCN5A (Nav1.5) | SkM2 (rat) | Skeletal muscle/ | M27902 |
|  | RH1 (rat) | Heart |  |
|  | H1 (human) | heart | M77235 |
| SCN8A (Nav1.6) | NaCh6 (rat) | CNS/PNS | L39018 |
|  | PN4a (rat) | CNS/PNS | AF049239A |
|  | Scn8a (mouse) | CNS | U26707 |
|  | ScnSa (human) | CNS | AF050736 |
|  | CerIII (guinea pig) | CNS | AF003373 |
| SCN9A (Nav1.7) | PN1 (rat) | PNS | U79568 |
|  | HNE-Na (human) | Thyroid | X82835 |
|  | Nas (rabbit) | Schwann cells | U35238 |
| SCN9A (Nav1.7) | SNS (rat) | PNS | X92184 |
|  | PN3 (rat) | PNS | U53833 |
|  | SNS (mouse) | PNS | Y09108 |
| SCN6A Nav2.1 | Na2.1 (human) | Heart, uterus, muscle | M91556 |
| SCN7A Nav2.2 | Na-G (rat) | Astrocytes | M96578 |
|  | SCL11 (rat) | PNS | Y09164 |
| nav2.3 | Na2.3 (mouse) | Heart, uterus muscle | L36179 |
| Nav3.1 |  |  |  |
| SCN1b Nβ1.1 | β-1 (rat) | CNS | M91808 |
|  | β-1 (human) | CNS | L10338 |
| SCN2b Nβ2.1 | β-2 (rat) | CNS | U37026 |
|  | β-2 (human) | CNS | AF007783 |

Potassium Channels

Voltage-dependent potassium channels repolarize nerve and muscle cells after action potential depolarization. They also play important regulatory roles in neural, muscular, secretory, and excretory systems.

A summary of the numerous potassium sub-types is presented in Table 3 below.

TABLE 3

Potassium Channel Sub-type Summary

| Channel Name | Sub-type/ Alternate names | Accession Number | Reference |
|---|---|---|---|
| ATP-regulated | rKir.1 (ROMK1) (rat) | U12541 | U.S. Pat. No. 5,356,775 |
| | hKirl.1 (ROMK1) (human) | | U.S. Pat. No. 5,882,873 |
| | Kirl.1 | U73191 | |
| | Kirl.3 | U73193 | |
| II. | Bcell | | U.S. Pat. No. 5,744,594 |
| III. | hβIR | | U.S. Pat. No. 5,917,027 |
| IV. | HuK$_{ATP}$-1 | | EP0 768 379A1 |
| Constitutively active | Kir2.1 (IRK1) | U12507 | U.S. Pat. No. 5,492,825 |
| | | | U.S. Pat. No. 5,670,335 |
| | Kir2.2 | X78461 | |
| | Kir2.3 | X78461 | |
| G-protein Regulated | Kir3.1 (GIK1, KGA) | U0171 | U.S. Pat. No. 5,728,535 |
| | Kir3.2 | U11859 | U.S. Pat. No. 5,734,021 |
| | Kir3.3 | U11869 | U.S. Pat. No. 5,744,324 |
| | Kir3.4 (CIR) | X83584 | U.S. Pat. No. 5,747,278 |
| | Kir4.1(BIR10) | X83585 | |
| | Kir5.1(BIR9) | X83581 | |
| | Kir6.1 | D42145 | |
| | Kir6.2 | D5081 | |
| | Kir7.1 | | EP0 922 763A1 |
| Voltage Regulated | | | |
| KCNA1 | hKv1.1 (RCK1, RBK1, MBK1, MK1, HuK1) | LO2750 | |
| KCNA2 | hKv1.2 (RBK2, RBK5, NGK1, HuKIV) | | |
| KCNA3 | Kv1.3 (KV3, RGK5, HuKiIII, HPCN3) | | |
| KCNA4 | Kv1.4 (RCK4, RHK1, HuKII) | | |
| KCNA5 | Kv1.5 (KV1, HPCN1, HK2) | | |
| KCNA6 | Kv1.6 (KV2, RCK2, HBK2) | | |
| KCNA7 | Kv 1.7 (MK6, RK6, HaK6) | | U.S. Pat. No. 5,559,009 |
| Kv2 (Shab) | | | |
| KCNB1 | Kv2.1(DRK1, mShab) | M64228 | |
| KCNB2 | Kv2.2 (CDRK1) | | U.S. Pat. No. 5,710,019 |
| | K channel 2 | | |
| Kv3 (Shaw) | | | |
| KCNB1 | Kv3.1 (NGK2) | | |
| KCNB2 | Kv3.2 (KshIIIA) | | |
| KCNB3 | Kv3.3 (KshIIID) | X607796 | |
| KCNB4 | Kv3.4 (Raw3) | | |
| Kv4 (Sh1) | | | |
| KCND1 | Kv4.1 (mShal, KShIVA) | M64226 | |
| KCND2 | Kv4.2 (RK5, Rat Shal1) | | |
| KCND3 | Kv4.3 (KShIVB) | | WO 99/41372 |
| | hKv5.1 (IK8) | | |
| | Kv6.1 (K13) | | |
| | Kv7 | | |
| | Kv8.1 | | |
| | Kv9 | | |
| Delayed Rectifier | KvLQT1 | AF000571 | U.S. Pat. No. 5,599,673 |
| | HERG (erg) | U04270 | WO 99/20760 |
| Calcium regulated | | | |
| Calcium Regulated Big | | | |
| | BKCa(hSLO) | U11717 | |
| | HBKb3 (β-subunit) | | WO 99/42575 |
| | Maxi-K | | U.S. Pat. No. 5,776,734 |
| | | | U.S. Pat. No. 5,637,470 |
| Calcium regulated | | | |
| Calcium regulated Small | | | |
| KCNN1 | SKCa1 | U69883 | |
| KCNN2 | SKCa2 | U69882 | |
| KCNN3 | SKCa3 | U69884 | |
| KCNN4 | SKCa4 (IKCa1) | | Muscle Nerve 1999 22(6) 742-50 |
| | TWIK1 | U33632 | |

Calcium Channels

Calcium channels are generally found in many cells where, among other functions, they play important roles in signal transduction. In excitable cells, intracellular calcium supplies a maintained inward current for long depolarizing responses and serves as the link between depolarization and other intracellular signal transduction mechanisms. Like voltage-gated sodium channels, voltage-gated calcium channels have multiple resting, activated, and inactivated states.

Multiple types of calcium channels have been identified in mammalian cells from various tissues, including skeletal muscle, cardiac muscle, lung, smooth muscle and brain, [see, e.g., Bean, B. P. (1989) Ann. Rev. Physiol. 51:367-384 and Hess, P. (1990) Ann. Rev. Neurosci. 56:337]. The different types of calcium channels have been broadly categorized into four classes, L-, T-, N-, and P-type, distinguished by current kinetics, holding potential sensitivity and sensitivity to calcium channel agonists and antagonists. Four subtypes of neuronal voltage-dependent calcium channels have been proposed (Swandulla, D. et al., Trends in Neuroscience 14:46, 1991).

Chloride Channels

Chloride channels are found in the plasma membranes of virtually every cell in the body. Chloride channels mediate a variety of cellular functions including regulation of transmembrane potentials and absorption and secretion of ions across epithelial membranes. When present in intracellular membranes of the Golgi apparatus and endocytic vesicles, chloride channels also regulate organelle pH. For a review, see Greger, R. (1988) Annu. Rev. Physiol. 50:111-122.

Three distinct classes of chloride channels are apparent based on their type of regulation and structural conformation, Table 3. The first class includes the GABA and Glycine receptor super families, the second class includes the CFTR (Cystic fibrosis Transmembrane Conductance Regulator) and the third class includes the voltage regulated chloride channels.

TABLE 4

Chloride Channel Sub-type Summary

| Channel Type | Sub-type | Tissue Distribution | Reference |
| --- | --- | --- | --- |
| Ligand gated | GABA_A Receptor family | CNS & PNS | Synapse 21, 189-274 (1995) |
| | Glycine Receptor family | CNS & PNS | Trends Neurosci. 14, 458-461 (1991) |
| cAMP regulated | CRTR | Epithelial tissues | Science 245, 1066-1073 (1989) |
| Voltage regulated | CIC-1 | Skeletal Muscle | Nature 354, 301-304 (1991) |
| | CIC-2 | Ubiquitous | Nature 356, 57-60 (1992) |
| | CIC-Ka | Kidney | J. Biol. Chem. 268, 3821-3824 (1993) |
| | CIC-Kb | Kidney | PNAS 91, 6943-6947 (1994) |
| | CIC-3 | Broad, e.g. kidney & brain | Neuron 12, 597-604 (1994) |
| | CIC-4 | Broad, e.g. kidney & brain | Hum. Nol. Genet. 3, 547-552 (1994) |
| | CIC-5 | Mainly kidney | J. Biol. Chem. 270, 31172-31177 91995) |
| | CIC-6 | Ubiquitous | FEBS Lett. 377, 15-20 (1995) |
| | CIC-7 | Ubiquitous | FEBS Lett. 377, 15-20 (1995) |

A neuromodulator used in the present disclosure can contain an amino acid sequence that is substantially similar to the amino acid sequence of any polypeptide described above. The neuromodular includes a polypeptide comprising an amino acid sequence having at least about 85%, at least about 89%, at least about 90%, at least about 95%, at least about 98%, or at least about 99%, amino acid sequence identity to a contiguous stretch of from about 50 amino acids (aa) to about 60 aa, from about 50 aa to about 65 aa, from about 50 aa to 70 aa, from about 70 aa to about 100 aa, from about 100 aa to about 125 aa, from about 125 aa to about 150 aa, from about 150 aa to about 175 aa, from about 175 aa to about 250 aa, from about 250 to 350 aa, or from about 400 up to the full length amino acid sequence of any neuromodulators described above. For example, a protein containing an amino acid sequence that is substantially similar to the amino acid sequence of an halorhodopsin polypeptide (P16102) includes a polypeptide comprising an amino acid sequence having at least about 85%, at least about 89%, at least about 90%, at least about 95%, at least about 98%, or at least about 99%, amino acid sequence identity to a contiguous stretch of from about 50 amino acids (aa) to about 60 aa, from about 50 aa to about 65 aa, from about 50 aa to 70 aa, from about 70 aa to about 100 aa, from about 100 aa to about 125 aa, from about 125 aa to about 150 aa, from about 150 aa to about 175 aa, from about 200 to 250, from about 250 up to the full length amino acid sequence set forth as the accession no. P16102 in the present disclosure.

The protein may lack at least 5 or up to at least 10 or more aa relative to a naturally-occurring full-length neuromodulator polypeptide. The protein may also contain the same or similar glycosylation pattern as those of a naturally-occurring neuromodulator protein.

Many DNA and protein sequences of neuromodulator proteins and nucleic acids are known in the art.

The proteins used in the method of the present disclosure include those containing contiguous amino acid sequences of any naturally-occurring neuromodulator, as well as those having 1, 2, 3, 4, 5, 6, 7, 8, 9, 10 or more amino acid substitutions, where the substitution can be a conservative amino acid substitution. By "conservative amino acid substitution" generally refers to substitution of amino acid residues within the following groups
  1) L, I, M, V, F;
  2) R, K;
  3) F, Y, H, W, R;
  4) G, A, T, S;
  5) Q, N; and 6) D, E Conservative amino acid substitutions in the context of a peptide or a protein disclosed herein are selected so as to preserve putative activity of the protein. Such presentation may be preserved by substituting with an amino acid with a side chain of similar acidity, basicity, charge, polarity, or size to the side chain of the amino acid being replaced. Guidance for substitutions, insertion, or deletion may be based on alignments of amino acid sequences of different variant proteins or proteins from different species. For example, neuromodulators used in the present disclosure may be humanized, modified for specific codon usage, and/or enchanced by substitution, deletion, insertion, and conjugation. Nucleotide and amino acid sequences of rhodopsins that have humanized or enhanced properties are known in the art. See, for example, Gradinaru V et al. (2008) *Brain Cell Biol.* 36:129-39 and Han X et al. (2007) *PLoS ONE* 2: e299. Details of other modifications and/or conjugation are discussed later below.

Targeted Expression

In the methods of the present disclosure, the first neuromodulator and the second neuromodulator are expressed at different locations in a neuron. Expression of the first and second neuromodulator at separate subcellular locations allows for the formation of center surround antagonism. For example, the first neuromodulator can be targeted to be expressed at the dendritic localization at synapses while the second neuromodulator is targeted to be expressed at the soma and/or proximal dendrites. In this manner, spatially distinct exhibitory and inhibitory zones can be created.

Targeting protein expression at a selective location can be mediated by fusion neuromodulator proteins. For example, a first neuromodulator can be fused to a targeting element. As used herein, "targeting element" is a protein that is known to be expressed only at a certain subcellular location but have decreased or no expression elsewhere in the cell. Targeting element also directs a localized expression of a protein fused to the targeting element. Ankyrin (e.g. ankyrin G, 33-residue repeat motif of ankyrin) is an example of a targeting element. It is a protein that is known to be expressed only at soma and/or proximal dendrites but have decreased or no expression at dendritic locations at synapses. Another example of a targeting element is postsynaptic density (PSD-95; DLG4) protein, which is expressed only at dendritic locations at synapses but decreased or no expression elsewhere in the neuronal cell. PSD-95 belongs to a protein superfamily named MAGUK that encompasses other proteins such as PSD-93, SAP97 and SAP102. These proteins are characterized by PDZ, SH3, GUK domains, and/or regions homologous of CaMKII, WW and L27 domains. These motifs and domains can also be used as targeting elements in the subject method outside the context of the proteins in which they naturally occur. In the subject methods, the second neuromodulator can be fused to a protein such as PSD-95.

Accordingly, in one example, the neuromodulaor proteins can be fused at the N-terminal end with motifs derived from either ankyrin and/or PSD-95. Any other proteins known in the art (e.g. gephyrin) that have an expression pattern restricted to a subcellular location can also be used as a targeting element to target expression of the neuromodulators. For sequences and details of such targeting elements, see, for example, Gai A. et al. (2008) *Cell* 135:1189-1200, Husseini et al. (2000) *J. Cell Biol.* 148:159-172, Giesemann et al. (2003) *J. Neurosci.* 23:8330-8339, and Craven et al. (2000) *J. Biol. Chem.* 275:20045-20051.

The fused segment can comprise an amino acid sequence having at least about 85%, at least about 89%, at least about 90%, at least about 95%, at least about 98%, or at least about 99%, amino acid sequence identity to a contiguous stretch of from about 10, 20, 25, 30, 35, 40, 50 amino acids (aa) to about 60 aa, from about 50 aa to about 65 aa, from about 50 aa to 70 aa, from about 70 aa to about 100 aa, from about 100 aa to about 125 aa, from about 125 aa to about 150 aa, from about 150 aa to about 175 aa, up to the full length amino acid sequence of the proteins that have targeted expression at a subcellular location.

Nucleic Acid Expressing a Neuromodulator

A wide range of host-vector systems suitable for the expression of the subject neuromodulator may be employed according standard procedures known in the art. See for example, Sambrook et al. 1989 *Current Protocols in Molecular Biology* Cold Spring Harbor Press, New York and Ausubel et al. 1995 *Current Protocols in Molecular Biology*, Eds. Wiley and Sons.

Methods for introduction of genetic material into host cells include, for example, viral transduction, transformation, electroporation, conjugation, calcium phosphate methods and the like. Nucleic acid of the present disclosure may also be delivered to a cell without the use of a vector, for example by electroporation of the nucleic acid. The method for transfer can be selected so as to provide for stable expression of the introduced neuromodulator-encoding nucleic acid. The polypeptide-encoding nucleic acid can be provided as an inheritable episomal element (e.g., plasmid) or can be genomically integrated. A variety of appropriate vectors for use in production of a polypeptide of interest are available commercially.

Numerous viral genomes useful in in vivo transformation and gene therapy are known in the art, or can be readily constructed given the skill and knowledge in the art. Included are replication competent, replication deficient, and replication conditional viruses. Viral vectors include adenovirus, mumps virus, a retrovirus, adeno-associated virus, herpes simplex virus (HSV), cytomegalovirus (CMV), vaccinia virus, and poliovirus, and non-replicative mutants/variants of the foregoing. In some embodiments, a replication-deficient virus is capable of infecting slowly replicating and/or terminally differentiated cells, since the respiratory tract is primarily composed of these cell types. For example, adenovirus efficiently infects slowly replicating and/or terminally differentiated cells. In some embodiments, the viral genome itself, or a protein on the viral surface, is specific or substantially specific for cells of the targeted cell. A viral genome can be designed to be target cell-specific by inclusion of cell type-specific promoters and/or enhancers operably linked to a gene(s) essential for viral replication.

Where a replication-deficient virus is used as the viral genome, the production of virus particles containing either DNA or RNA corresponding to the polynucleotide of interest can be produced by introducing the viral construct into a recombinant cell line which provides the missing components essential for viral replication and/or production. Preferably, transformation of the recombinant cell line with the recombinant viral genome will not result in production of replication-competent viruses, e.g., by homologous recombination of the viral sequences of the recombinant cell line into the introduced viral genome. Methods for production of replication-deficient viral particles containing a nucleic acid of interest are well known in the art and are described in, for example, Rosenfeld et al., *Science* 252:431-434, 1991; Rosenfeld et al., *Cell* 68:143-155, 1992 (adenovirus); U.S. Pat. No. 5,139,941 (adeno-associated virus); U.S. Pat. No. 4,861,719 (retrovirus); and U.S. Pat. No. 5,356,806 (vaccinia virus). Methods and materials for manipulation of the mumps virus genome, characterization of mumps virus genes responsible for viral fusion and viral replication, and the structure and sequence of the mumps viral genome are described in Tanabayashi et al., J. Virol. 67:2928-2931, 1993; Takeuchi et al., Archiv. Virol., 128:177-183, 1993;

Tanabayashi et al., Virol. 187:801-804, 1992; Kawano et al., Virol., 179:857-861, 1990; Elango et al., J. Gen. Virol. 69:2893-28900, 1988.

In an example, the neuronal cell specific vector is a recombinant herpes simplex virus, such as HSV-1. The recombinant herpes simplex virus may be debilitated for growth via non-silent insertion, substitution, or deletion of a nucleotide sequence in at least one non-essential gene of the herpes simplex virus. In a related embodiment, the recombinant herpes simplex virus may further comprise a non-silent insertion, substitution, or deletion of a nucleotide sequence in at least one essential gene of the herpes simplex virus. In one embodiment, the herpes simplex virus lacks one expressible $\gamma_L 34.5$ gene, a non-essential gene. In a further embodiment, the recombinant herpes simplex lacks both expressible $\gamma_L 34.5$ genes.

Vectors can provide for extrachromosomal maintenance in a host cell or can provide for integration into the host cell genome. The expression vector provides transcriptional and translational regulatory sequences, and may provide for inducible or constitutive expression, where the coding region is operably linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7, and the like). The subject method can use cell-specific promoters to drive expression of the neuromodulator only in cells to be transduced (e.g., forebrain neurons, retinal ganglion cells, etc.). One example of a promoter that can be used is CaMKII promoter.

Expression constructs generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selectable genes are well known in the art and will vary with the host cell used.

Details of how targeted protein expression construct can be built is shown in FIG. 1 and described in the example section below. As seen in FIG. 1, the expression can be driven by a promoter (e.g. CaMKII) and the neuromodulators channelrhodopsin-2 (ChR2) and enhanced halorhodopsin (eNpHR) are fused to targeting elements such as ankyrin$_G$ and PSD-95. The neuromodulator can optionally be fused to an element to enhance expression (e.g. woodchuck hepatitis post-transcriptional regulatory element) and a fluorescent protein (e.g. cherry fluorescent protein) for visualization.

Protein Modifications

The present disclosure provides methods of using but not limited to any of the neuromodulator proteins described above. The neuromodulator used can be provided as proteins that are modified relative to the naturally-occurring protein. Purposes of the modifications may be to increase a property desirable in a protein designed to have enhanced sensitivity, robust expression, prolonged half-life, and/or enhanced detection, and the like. As noted above, the neuromodulator is also fused to targeting elements.

One way to modify a subject protein is to conjugate (e.g. link) one or more additional elements at the N- and/or C-terminus of the protein, such as another protein (e.g. having an amino acid sequence not present in a naturally-occurring version of the subject neuromodulator) and/or a carrier molecule. Thus, a protein can be provided as fusion proteins with a polypeptide(s) derived from a neuromodulator polypeptide.

Conjugate modifications to proteins may result in a protein that retains the desired activity, while exploiting properties of the second molecule of the conjugate to impart and/or enhances certain properties (e.g. desirable for therapeutic uses). For example, the polypeptide may be conjugated to a molecule, e.g., to facilitate solubility, storage, half-life, reduction in immunogenicity, controlled release in tissue or other bodily location (e.g., blood or other particular organs, etc.).

Other features of a conjugated protein may include one where the conjugate reduces toxicity relative to unconjugated protein. Another feature is that the conjugate may target a type of cell or organ, and/or subcellular location more efficiently than an unconjugated material. The protein can optionally have attached a peptide, polypeptide, and/or biomolecule to further counter the causes or effects associated with disorders of retinal degeneration, and/or can optionally be modified to provide for improved pharmacokinetic profile.

Where the proteins are to be detected in an assay, the subject proteins may also contain a detectable label, e.g., an enzyme which generates a detectable product (e.g., luciferase, (3-galactosidase, horse radish peroxidase, alkaline phosphatase, and the like), a fluorescent protein, a chromogenic protein, dye (e.g., fluorescein isothiocyanate, rhodamine, phycoerythrin, and the like); fluorescence emitting metals, e.g., $^{152}$Eu, or others of the lanthanide series, attached to the protein through metal chelating groups such as EDTA; chemiluminescent compounds, e.g., luminol, isoluminol, acridinium salts, and the like; bioluminescent compounds, e.g., luciferin; fluorescent proteins; and the like. Indirect labels include antibodies specific for a subject protein, wherein the antibody may be detected via a secondary antibody; and members of specific binding pairs, e.g., biotin-avidin, and the like.

Any of the above elements that are used to modify the subject proteins may be linked to the polypeptide via a linker, e.g. a flexible linker. Where a subject protein is a fusion protein comprising a neuromodulator polypeptide and a heterologous fusion partner polypeptide, a subject fusion protein can have a total length that is equal to the sum of the neuromodulator polypeptide and the heterologous fusion partner polypeptide.

Linkers suitable for use in modifying the proteins of the present disclosure include "flexible linkers". If present, the linker molecules are generally of sufficient length to permit the protein and a linked carrier to allow some flexible movement between the protein and the carrier. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)n, glycine-serine polymers (including, for example, (GS) n, GSGGSn (SEQ ID NO: 1) and GGGSn (SEQ ID NO: 2), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited GGSG (SEQ ID NO: 3), GGSGG (SEQ ID NO: 4), GSGSG (SEQ ID NO: 5), GSGGG (SEQ ID NO: 6), GGGSG (SEQ ID NO: 7), GSSSG (SEQ ID NO: 8), and the like. The ordinarily skilled artisan will recognize that design of a peptide conjugated to any elements described above can include linkers that are all or partially flexible, such that the linker can include a flexible linker as well as one or more portions that confer less flexible structure.

Neuronal Cells

The present invention provides the use of a first and a second neuromodulators for inducing photosensitivity in one or more neuronal cell, in which the neuromodulators have a different targeted subceullar expression and opposite excitatory/inhibitory potentiating function. Because of the formation of the center-surround antagonism, the transduced neuronal cell can then process light information to detect edges.

The methods of the present disclosure include the use of the neuromodulators for inducing photosensitivity in one or more neuronal cell (e.g. RGC) in vivo (for example, in an individual) and/or ex vivo (for example, outside the body of an individual) and/or in vitro (for example, in a cell culture).

The neuronal cells usually have no or low photosensitivity. The neuronal cells can be in a retina that has little or no functional photoreceptors. The neuronal cells may be proximal or distal to the degeneration that has occurred to photoreceptors and/or bipolar cells. The method of the present disclosure can be used in which the neuronal cell is a retinal ganglion cell (RGC).

Other types of neuronal cell other than a retinal ganglion cell (RGC) (e.g. amacrine) could be used in the methods of the present disclosure. Neuronal cells encompass cells of the nervous system of a mammal, particularly cells of the central nervous system (CNS) which lie within the blood brain barrier and/or the blood-retina barrier, especially cells of the brain (e.g. neurons from spinal cord, cerebellum, basal ganglia, thalamus, hippocampus, substantia nigra, neocortex, endothelial cells derived from the neural crest, foetal neurons, neuronal multipotent cell lines, adrenal chromaffin cells, striatum, glial cells, myoblasts, or fibroblasts).

Other cells in which the subject method can be used encompass primary and transformed cell cultures prepared from neural tissue according to methods known in the art, and/or are commercially available. For example, mouse neuroblastoma-2a (Neuro-2a) cell line can be obtained from the ATCC (American Type Culture Collection; European distributors http://www.Igcpromochem.com/atcc, ATCC number CCL-131).

The specific application of the subject method will depend upon the cell type targeted and the host employed. For example, the type of cell-specific and/or tissue-specific promoters may be chosen depending on the desired cells to be treated.

A number of techniques known to those in the art could be used to induce activity of neuromodulators in selected populations of specific cell types. For example, a neuromodulator, or a nucleic acid encoding thereof, could be introduced into specific tissues and/or cell types in vivo and/or in vivo by local inoculation with a viral and/or plasmid expression construct.

A gene-specific promoter could be used to direct expression of a nucleic acid encoding a photoactivator in cells in which that promoter is active. For example, expression could be restricted to retinal ON bipolar cells by using the cell-specific mGluR6 promoter. DNA comprising a cell-specific promoter and a nucleic acid encoding a photoactivator could be introduced into cells in plasmid and/or viral vectors using techniques known in the art.

Where the method is applied to non-human animals, transgenic animals could be generated in which the neuromodulators are expressed in specific cell types in that animal. Techniques for the generation of a number of species of transgenic animal (including, for example, zebrafish, drosophila and mouse and rat species) are well known to those skilled in the art. Nucleic acid constructs that are suitable for the introduction of a nucleic acid of interest are known and can be randomly incorporated into the genome of cells of a transgenic animal or introduced at specific loci into the genome of cells of a trans genic animal by homologous recombination ('knock-ins').

A nucleic acid comprising a promoter and the nucleic acid of interest may be introduced into the genome of cells of the transgenic animal flanked by enzyme recognition sites that allow the nucleic acid to be selectively spliced out of the genome of cells of the transgenic animal. Such systems are well known in the art and allow a nucleic acid of interest to be turned "on" and "off" in selected cell types in the transgenic animal. A commonly used system is the "lox" system, wherein the nucleic acid of interest is flanked by recognition sites (termed "lox" sites) that can be recognised by the cre recombinase enzyme.

Compositions

The embodiments further provide compositions comprising one or more subject neuromodulators (e.g. two) to be used in the methods of the present disclosure. The neuromodulator is present in the subject composition as a protein and/or a nucleic acid encoding thereof. In many examples of the subject method, the composition containing a neuromodulator refers to a composition containing a nucleic acid construct encoding a neuromodulator. For example, the construct contains fusions that enable targeted expression so that a first neuromodualtor is expressed at a subcellular location different from a second neuromodulator.

Compositions comprising a subject neuromodulator can include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-morpholino)ethanesulfonic acid (MES), 2-(N-morpholino)ethanesulfonic acid sodium salt (MES), 3-(N-Morpholino)propanesulfonic acid (MOPS), N-tris[hydroxymethyl]methyl-3-aminopropanesulfonic acid (TAPS), etc.; a solubilizing agent; a detergent, e.g., a non-ionic detergent such as Tween-20, Nonidet-P40, etc.; a protease inhibitor; and the like.

Pharmaceutical Compositions

The embodiments provide pharmaceutical compositions comprising a neuromoduatlor. The pharmaceutical composition can be suitable for administering to an individual in need thereof.

A pharmaceutical composition comprising a one or more neuromoduatlors may be administered to a patient alone, or in combination with other supplementary active agents. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilisate, tablet, pill, pellet, capsule, powder, syrup, elixir or any other dosage form suitable for administration.

A pharmaceutical composition comprising a subject neuromodulator can optionally include a pharmaceutically acceptable carrier(s) that facilitate processing of an active ingredient into pharmaceutically acceptable compositions. As used herein, the term "pharmacologically acceptable carrier" refers to any carrier that has substantially no long-term or permanent detrimental effect when administered and encompasses terms such as "pharmacologically acceptable vehicle, stabilizer, diluent, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., distilled, deionized water, saline; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in "Pharmaceutical Dosage Forms and Drug Delivery Systems" (Howard C. Ansel et al., eds., Lippincott Williams & Wilkins Publishers, $7^{th}$ ed. 1999); "Remington: The Science and Practice of Pharmacy" (Alfonso R. Gennaro ed., Lippincott, Williams & Wilkins, $20^{th}$ 2000); "Goodman & Gilman's The Pharmacological Basis of Therapeutics" Joel G. Hardman et al., eds., McGraw-Hill Professional, 10.sup.th ed. 2001); and "Handbook of Pharmaceutical Excipients" (Raymond C. Rowe et al., APhA Publications, $4^{th}$ edition 2003).

A subject pharmaceutical composition can optionally include, without limitation, other pharmaceutically acceptable components, including, without limitation, buffers, preservatives, tonicity adjusters, salts, antioxidants, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate and a stabilized oxy chloro composition, for example, PURITE™. Tonicity adjustors suitable for inclusion in a subject pharmaceutical composition include, without limitation, salts such as, e.g., sodium chloride, potassium chloride, mannitol or glycerin and other pharmaceutically acceptable tonicity adjustor. It is understood that these and other substances known in the art of pharmacology can be included in a subject pharmaceutical composition.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

A subject neuromodulator can be formulated with one or more pharmaceutically acceptable excipients. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods (described below), a subject neuromodulator may be administered to the host using any convenient means capable of resulting in the desired improvement in sight restoration, for example. Thus, a subject neuromodulator can be incorporated into a variety of formulations for therapeutic administration. More particularly, a subject neuromodulator can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

A subject neuromodulator can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject neuromodulator can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

Unit dosage contains a predetermined amount of the composition containing one or more neuromodulators. Similarly, unit dosage forms for injection or intravenous administration may comprise a subject neuromodulator in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject neuromodulator calculated in an amount sufficient to produce the desired effect in association with a pharmaceutically acceptable diluent, carrier or vehicle. The specifications for a subject neuromodulator depend on the particular compound employed and the effect to be achieved, and the pharmacodynamics associated with each compound in the host.

A subject neuromodulator can be administered as injectables. Injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

In some embodiments, a subject neuromodulator is delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Utility

A subject neuromodulator, a subject light-regulated polypeptide, a subject cell, and a subject method of modulating receptor function, are useful in a wide variety of research applications, pharmaceutical applications, screening assays, therapeutic applications, and the like.

Research Applications

The methods of the present disclosure can be useful in studies of cell function, in studies of visual processing, visual-induced behaviros in an organism, and the like.

Therapeutic Applications

A subject neuromodulator of protein function is suitable for use in a variety of therapeutic applications. A subject neuromodulator is useful in restoring light sensitivity to a retina that has reduced light sensitivity.

In particular, the present disclosure relates to compositions and methods for restoring sight and/or alleviating blindness in an individual, particularly by using a neuromodulator to induce photosensitivity in one or more retinal ganglion cells (RGC).

The eyes are complex sense organs comprising a layer of receptors, a lens system that focuses light on these receptors and a system of nerves that conducts impulses from the receptors to the brain. The visual receptors (known as rods and cones) and four types of neurons (bipolar cells, ganglion cells. horizontal cells and amacrine cells) are contained in the retina at the back of the eye. The rods and cones synapse with bipolar cells, which in turn synapse with ganglion cells, the axons of which converge and leave the eye as the optic nerve.

Hereditary and sporadic degenerative diseases affecting rod and cone photoreceptors are the second largest cause of blindness in the developed world. Whilst these conditions may be characterised by a catastrophic loss of light-sensitive rod and cone cells in the outer retina of the eye, sufferers generally retain a normal optic apparatus and a viable population of the retinal ganglion cells that form the optic nerve with intact projections to the higher visual areas.

Accordingly, the present methods can be used as clinical interventions aimed at overcoming the primary lesion (i.e. the loss of photoreceptive capacity) and improve visual function.

The method can involve administering to an individual in need thereof an effective amount of a subject neuromodulator of protein function locally, e.g., in or around the eye.

A pharmaceutical composition comprising a subject neuromodulator that confers light sensitivity on a cell can be delivered to the eye through a variety of routes. A subject pharmaceutical composition may be delivered intraocularly, by topical application to the eye or by intraocular injection into, for example the vitreous or subretinal (interphotoreceptor) space. Alternatively, a subject pharmaceutical composition may be delivered locally by insertion or injection into the tissue surrounding the eye. A subject pharmaceutical composition may be delivered systemically through an oral route or by subcutaneous, intravenous or intramuscular injection. Alternatively, a subject pharmaceutical composition may be delivered by means of a catheter or by means of an implant, wherein such an implant is made of a porous, non-porous or gelatinous material, including membranes such as silastic membranes or fibers, biodegradable polymers, or proteinaceous material. A subject pharmaceutical composition can be administered prior to the onset of the condition, to prevent its occurrence, for example, during surgery on the eye, or immediately after the onset of the pathological condition or during the occurrence of an acute or protracted condition.

The effects of therapy for an ocular disorder as described herein can be assessed in a variety of ways, using methods known in the art. For example, the subject's vision can be tested according to conventional methods. Such conventional methods include, but are not necessarily limited to, electroretinogram (ERG), focal ERG, tests for visual fields, tests for visual acuity, ocular coherence tomography (OCT), Fundus photography, Visual Evoked Potentials (VEP) and Pupillometry. In general, the embodiments provide for maintenance of a subject's vision (e.g., prevention or inhibition of vision loss of further vision loss due to photoreceptor degeneration), slowing progression of vision loss, or in some embodiments, providing for improved vision relative to the subject's vision prior to therapy.

Conditions that are amenable to treatment according to the methods of the present disclosure include, but are not necessarily limited to, diabetic retinopathy, age-related macular degeneration (AMD or ARMD) (wet form); dry AMD; retinopathy of prematurity; retinitis pigmentosa (RP); diabetic retinopathy; and glaucoma, including open-angle glaucoma (e.g., primary open-angle glaucoma), angle-closure glaucoma, and secondary glaucomas (e.g., pigmentary glaucoma, pseudoexfoliative glaucoma, and glaucomas resulting from trauma and inflammatory diseases).

Other conditions amenable to treatment according to the methods of the present disclosure include, but are not necessarily limited to, retinal detachment, age-related or other maculopathies, photic retinopathies, surgery-induced retinopathies, toxic retinopathies, retinopathy of prematurity, retinopathies due to trauma or penetrating lesions of the eye, inherited retinal degenerations, surgery-induced retinopathies, toxic retinopathies, retinopathies due to trauma or penetrating lesions of the eye.

Inherited conditions that can be treated according to the methods of the present disclosure include, but are not necessarily limited to, Bardet-Biedl syndrome (autosomal recessive); Congenital amaurosis (autosomal recessive); Cone or cone-rod dystrophy (autosomal dominant and X-linked forms); Congenital stationary night blindness (autosomal dominant, autosomal recessive and X-linked forms); Macular degeneration (autosomal dominant and autosomal recessive forms); Optic atrophy, autosomal dominant and X-linked forms); Retinitis pigmentosa (autosomal dominant, autosomal recessive and X-linked forms); Syndromic or systemic retinopathy (autosomal dominant, autosomal recessive and X-linked forms); and Usher syndrome (autosomal recessive).

In some embodiments, a subject pharmaceutical composition is administered (e.g., injected) at or near a nerve. Thus, in some embodiments, a subject pharmaceutical composition is formulated for injection at or near a nerve. For example, for oral surgery, a subject pharmaceutical composition is injected at or near a nerve in gum tissue.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Materials and Methods

The following methods and materials were used in the Examples below.

Preparation of Whole Mount Retina. New Zealand white rabbits (2.5 kg) were anesthetized and euthanized in accordance with the ARVO Statement for the Use of Animals in Ophthalmic and Vision Research and protocols approved by the Office of Laboratory Animal Care at the University of California, Berkeley. The eyes were quickly enucleated and placed in physiological saline solution (1.9 g/L sodium bicarbonate (EMD), 0.05 g/L kanamyacin sulfate (Invitrogen), 8.8 g/L AMES powder (Sigma) and bubbled with 95% oxygen, 5% carbon dioxide (BIOBLEND, Praxair). Eyes were dissected in dim red light by first removing the vitreous, then the periphery was cut away to preserve the visual streak, a region approximately 3 mm by 4 mm. The visual streak was cut into thirds, then adhered to Millipore filter discs as described (Koizumi et al. (2007) *PLoS One* 2:e221), and cultured for 24-72 hours following biolistic gene transfer. During recording, a constant perfusion of AMES solution, bubbled with 95% oxygen and 5% carbon dioxide, was provided to the chamber at a rate of 6 mL/min. Photoreceptor-mediated light responses were blocked via bath perfusion of 20 um 1-AP4 (dl-2-amino-4-phosphono-butyric acid), 10 um CNQX (6-cyano-7-nitroquinoxaline-2,3-dione), and 10 um CPP [(±)-3-(2-Carboxypiperazin-4-yl)propyl-1-phosphonic acid]. All chemicals were purchased from Tocris except where indicated. No all-trans-retinal was provided during recording.

Plasmid DNA construction and Biolistic Gene Transfer DNA constructs were generated using standard molecular biology protocols. All constructs were fully sequenced to check for accuracy of the cloning procedure. The plasmid (FCK-hChR2-mCherry) containing the humanized channel-rhodopsin-2-mCherry fusion expressed by the CaMKIIa promoter was a gift of Ed Boyden. The plasmid (Lenti-CaMKIIa-eNpHR-EYFP—WPRE) containing the enhanced halorhodopsin-eYFP fusion expressed by the CaMKIIa promoter was a gift of Karl Deisseroth. The N terminus of the Ankyrin$_G$ rat 270 kD isoform (AF102552) corresponding to position 1-2512 was synthesized. The N terminus of the rat PSD-95 cDNA corresponding to position 1-2235 was subcloned from GWPSD-95mEGFP, a gift of Don Arnold. Fusions of hChR2 or eNpHR with Ankyrin$_G$ or PSD-95 were generated using high fidelity PCR and standard subcloning techniques. Plasmid sequences are available upon request. hChR2 and eNpHR plasmids were co-precipitated in equimolar ratios onto 1.6 um gold microparticles and delivered to ex-vivo rabbit retina whole mount cultures as described (Koizumi et al., 2007).

Confocal Microscopy. Fluorescently tagged opsins co-expressed in ganglion cells were imaged in live retinal explant cultures. Images were acquired with an Olympus FV1000/BX61 fixed-stage upright laser scanning confocal microscope equipped with argon and helium-neon lasers and a 20×/0.95 water immersion objective lens. Image reconstructions were performed using Olympus Fluoview software.

Visual Stimulation for Retinal Recordings. hChR2 and eNpHR were activated with full-field illumination generated by a 120 W metal halide lamp-based epifluorescent illuminator (EXFO Xcite 120, EXFO Photonic Solutions Inc., Quebec, Canada) controlled with a VMM-D1 high-speed shutter (Uniblitz, Rochester, N.Y.). Patterned illumination was generated by a 360 W (5000 lumens) DLP projector (SP870, BenQ USA, Irvine, Calif.) projected onto the retina via custom optics. Full-field and patterned illumination were controlled with custom-made software (Matlab, Mathworks Inc.; Labview, National Instruments). Ganglion cells expressing hChR2 and eNpHR were activated with illumination (460 nm+/−40 nm, 560+/−40 nm) intensities ranging from 0.1-10 mW/mm$^2$.

Patch Clamp Electrophysiology. Whole cell patch clamp was used to examine the excitatory and inhibitory currents in ganglion cells. Extracellular recordings were used to examine spiking Patch pipettes were pulled from thin walled glass tubes with a filament (1.5 mm diameter, 4 in long, World Precision Instrument) using a pipette puller (Sutter Instruments, Novato, Calif.). The intracellular solution contained the following: 129 mM K-gluconate, 10 mM HEPES, 10 mM KCl, 4 mM MgATP, 0.3 mM $Na_3GTP$, titrated to pH 7.2; extracellular solution: 125 mM NaCl, 2 mM KCl, 3 mM $CaCl_2$, 1 mM $MgCl_2$, 30 mM glucose, and 25 mM HEPES, titrated to pH 7.3. A small tear was made in the inner limiting membrane with a glass electrode under visually guided control with a micromanipulator to allow access to the ganglion cell layer. A patch pipette (6-8 MΩ resistance) was brought to the soma of fluorescently labeled ganglion cells by visual guidance, a 1.5-2.5 GΩ seal was achieved prior to breaking in with increasing voltage steps (increasing in 50 mV increments from 50 mV to 250 mV). The correction for junction potential was 5 mV. An Axopatch 200-B (Axon Instruments, Inc.) amplifier was used to voltage and current clamp the cell. Reversal potentials were measured by holding the cell at a range of potentials from −60 mV to +20 mV. Current and voltage recordings were digitized and sampled at 2 kHz. All signals were post-analyzed with custom-made software (Matlab, Mathworks Inc.; Labview. National Instruments).

Statistical Analysis. Statistical significance was determined using a one-tailed heteroscedastic Student's t-test. Error bars represent standard error of the mean.

Computer Based Retinal Simulation. Input and output simulations of human midget ganglion cells including Gaussian blur functions, color processing, and the hexagonal sampling mosaic were generated using custom-made code (Matlab, Mathworks Inc.), Photoshop CS4 (Adobe Systems Incorporated), and Dream Suite Bonus (Auto FX). All simulations were based on a 640×480 pixel image that subtends 30×22.5° (9×6.75 mm) on the central retina and conversion factors of 300 µm/degree and 14.06 µm/pixel were used.

Overview of Examples

The insertion of optical neuromodulators into normally non-photosensitive retinal neurons is a promising approach for restoring sight to profoundly blind individuals. Various strategies have recently been implemented including the delivery of the directly photosensitive cation channel channelrhodopsin-2 (ChR2), synthetically engineered potassium (SPARK) and glutamate (LiGluR) channels, and the G-protein coupled receptor melanopsin to normally non-photosensitive bipolar, amacrine, and ganglion cells. These pioneering studies demonstrated the feasibility of restoring light sensitivity to a degenerate retina, that light-driven information is transmitted to higher visual centers, and that simple visually-guided behaviors can be mediated through these prosthetic interventions.

A fundamentally different approach was developed that has the benefits of retaining crucial retinal information processing capability while being independent of the state of inner retinal circuit remodeling during degeneration. An excitatory center and a truly antagonistic surround were genetically reconstructed directly at the ganglion cell membrane by targeting antagonistic opsins to discrete subcellular domains. The visual image with differential Gaussian blurring was preprocessed at each wavelength to approximate the relative dimensions of the antagonistic receptive field center and surround. Direct measurement and simulation demonstrated that dynamic control of edge extraction can be attained by spatio-chromatic image preprocessing of excitatory and inhibitory input channels.

Example 1

Targeting of Antagonistic Opsins to Separate Subcellular Domains

Proper synaptic development and function require precise localization of proteins to specialized subcellular and plasma membrane domains. Some classic examples are the accumulation of $Na^+$ channels at nodes of Ranvier in association with the cytoskeletal protein ankyrin, the clustering of glycine receptors at inhibitory synapses in association with gephyrin, and accumulation of NMDA receptors and post-synaptic signaling cascades at excitatory synapses via post-synaptic density (PSD) proteins. Using these intrinsic localization mechanisms to create spatially distinct excitatory and inhibitory zones, we genetically targeted humanized channelrhodopsin-2 (hChR2), an excitatory cation channel, and enhanced halorhodopsin (eNpHR), an inhibitory chloride pump, to somatic or dendritic compartments. N-terminal fusions were constructed with these opsins and motifs derived from ankyrin$_G$ or postsynaptic density (PSD-95) proteins (FIGS. 1A-1F).

Ankyrins are membrane-associated proteins that bind voltage-sensitive sodium channels and couple them to the spectrin—actin network and may also form lateral complexes involving L1 cell adhesion molecules (CAM) and ion channels (Bennett et al. (1993) *Annu Rev Cell Biol* 9:27-66; Srinivasan et al. (1988) *Nature* 333:177-180). The 480/270-kD alternatively spliced isoforms of ankyrin$_G$ colocalize with voltage-sensitive sodium channels at nodes of Ranvier (Kordeli et al. (1995) *J Biol Chem* 270:2352-2359) and in axons of cultured retinal ganglion cells (Kaplan et al. (1997) *Nature* 386:724-728). The serine-rich domain, present in 480- and 270-kD ankyrin$_G$ polypeptides, contributes to restriction of ankyrin$_G$ to somatic and proximal axon segments (Zhang et al. (1998) *J Cell Biol* 142:1571-1581). When fused with hChR2 or eNpHR, the 270-kD Ankyrin$_G$ polypeptide was effective at localizing these opsins to the soma and proximal dendrites of ganglion cells (FIGS. 1G, 1K), while untargeted opsins diffused throughout the plasma membrane (FIGS. 1M, 1N).

At excitatory synapses, glutamate receptors are clustered at the postsynaptic density (PSD), a thickening of the cytoskeleton beneath the plasma membrane. PSD-95 protein in brain and in transfected COS cells partitions as an integral membrane protein, a behavior that relies on the N terminus of the protein (Topinka et al. (1998) *Neuron* 20:125-134). In the retina, PSD-95 is known to organize NMDA receptors in ganglion cells, and this synaptic structure is particularly important for the cone bipolar cell pathway. A fusion protein was therefore created consisting of the N terminus of PSD-95 and either hChR2 or eNpHR for dendritic localization at synapses in ganglion cells. N-terminal fusions of PSD-95 with hChR2 or eNpHR concentrated these opsins in the dendritic regions of ganglion cells (FIGS. 1H, 1J).

Example 2

HChR2 and eNpHR Behave Antagonistically at Normal Resting Potentials

In order for genetically reconstructed center-surround antagonism to function effectively in a neuron, the opsins must generate opposing currents at physiologically-negative resting potentials and their chromatic sensitivity must be distinct. This antagonistic interaction was verified by whole-cell patch clamp recording from transfected ganglion cells in intact retina while perfusing a cocktail of CPP, 1-AP4, and CNQX to disrupt NMDA, metabotropic, and ionotropic glutamate receptor mediated currents derived from the photoreceptor to bipolar cell pathway. Following biolistic delivery (24-72 hrs) of PSD-95 and ankyrin$_G$ opsin fusions, we measured the electrophysiological properties of these transfected retinal ganglion cells in response to full field illumination. Currents were recorded from ganglion cells expressing both hChR2 and eNpHR while voltage clamped at negative resting potentials (−60 mV) during transient illumination with 460 nm or 560 nm light. At negative clamped potentials, blue (460 nm) light elicited hChR2-mediated excitatory inward currents while yellow (560 nm) light drove eNpHR-mediated outward inhibitory currents (FIG. 2A).

Figure 2:
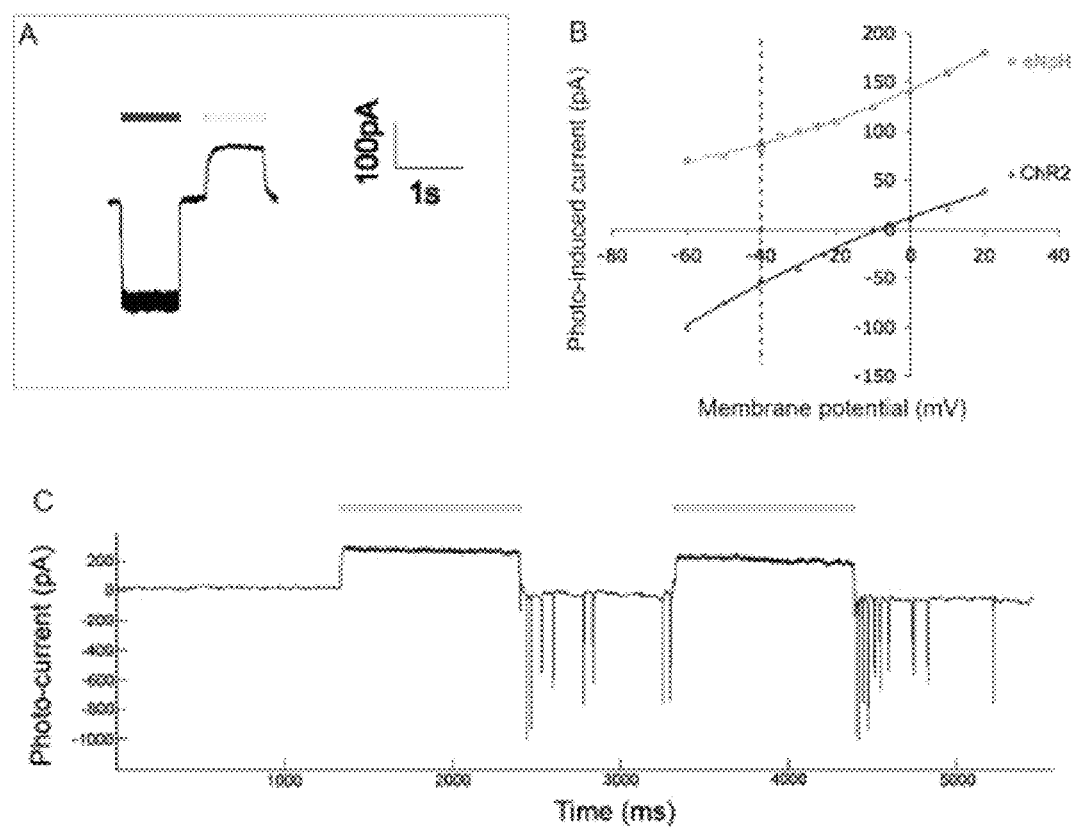
FIG. 2. hChR2 and eNpHR drive opposing currents in ganglion cells. (A) Representative whole cell voltage clamp recording (−60 mV) of ganglion cells expressing PSD95-hChR2 and Ankyrin$_G$-eNpHR reveals inward excitatory and outward inhibitory currents elicited by consecutive blue (460 nm) and yellow (560 nm) full-field illumination (n=6). (B) Current-voltage (I-V) relationship for both hChR2 (dark) and eNpHR (light) demonstrates that at normal resting potentials (−40 mV dashed line) for ganglion cells, hChR2 drives inward excitatory currents and eNpHR drives opposing outward inhibitory currents (n=10). The reversal potential for hChR2 is approximately 10 mV, while eNpHR reverses at −200 mV (via extrapolation). (C) eNpHR drives a strong hyperpolarization during yellow flash (light bar), followed immediately by rebound depolarization and transient action potentials (n=7). The action potentials appear because they could not be eliminated by the patch clamp.

The voltage was next stepped in 10 mV increments to progressively more positive membrane potentials to determine the current-voltage (I-V) relationship. hChR2 drives inward currents at physiological resting potentials (−40 mV dashed line) with a reversal potential near 10 mV (FIG. 2B). Importantly, at the same resting potential, eNpHR drives outward currents with a reversal potential near −200 mV (FIG. 2B). Therefore, at physiologically relevant resting potentials between −40 mV and −10 mV, these two opsins generate opposing currents that can be driven by spectrally distinguishable illumination when co-expressed in retinal neurons. At −40 mV, full field yellow illumination drives eNpHR-mediated outward inhibitory currents followed immediately by an after-hyperpolarization and rebound spikes (FIG. 2C). This ganglion cell behaves much like an OFF-center cell, signaling light decrements with a transient spike train.

Example 3

PSD95-hChR2 Enables Robust Spiking in RGCs

Figure 3:
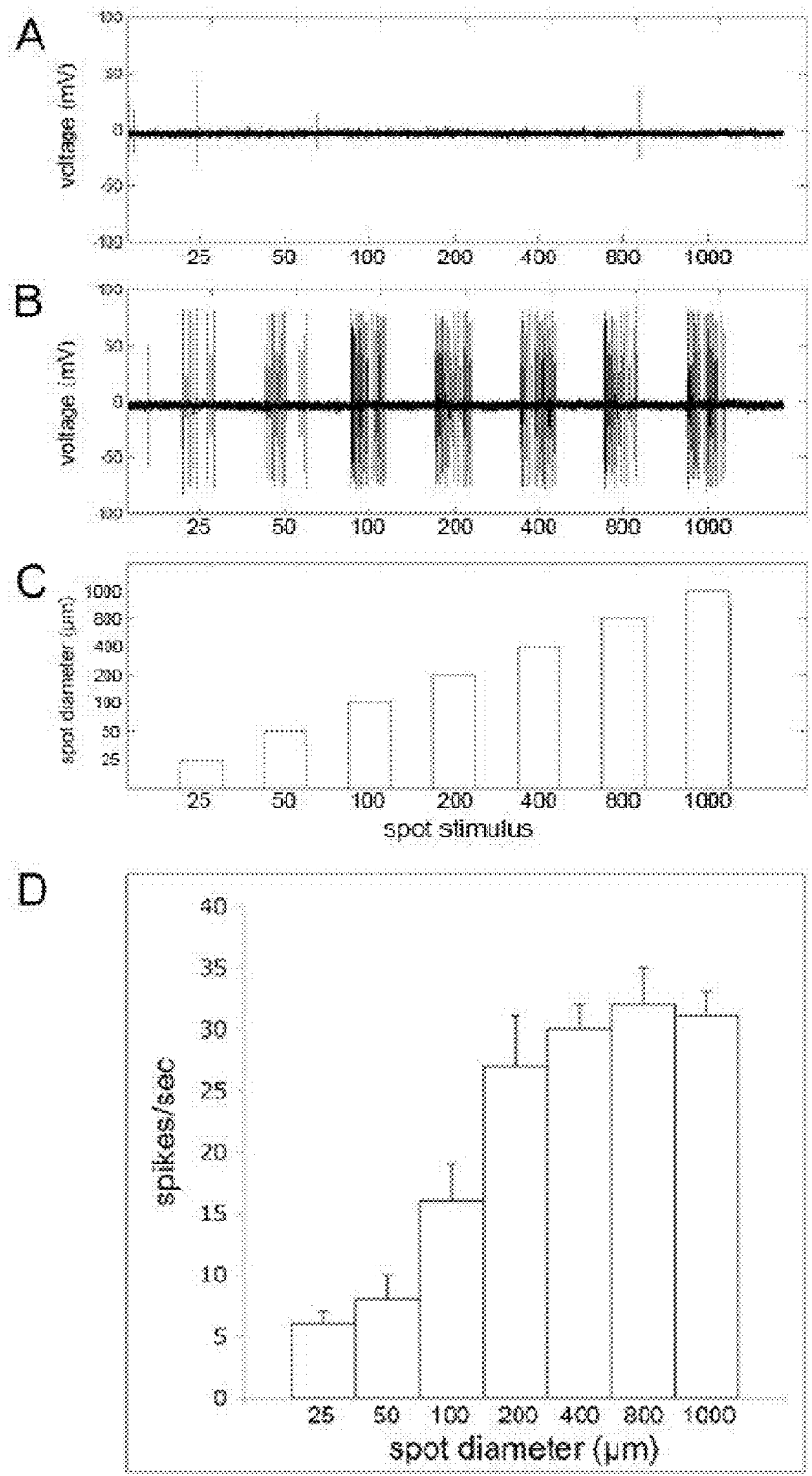
FIG. 3. PSD95-hChR2 mediates spiking in ganglion cells. Extracellular spike recordings from whole mount rabbit retina in the presence of 1-AP4 (20 µm), CPP (10 µm), and CNQX (10 µm) cocktail designed to block all photoreceptor-driven synaptic transmission to ganglion cells. Spot stimuli ranging from 25-1000 µm diameter were flashed for 500 ms. (A) White spots (0.012 mW/mm$^2$) fail to drive ganglion cell spikes due to the presence of drug cocktail (n=17). This illumination intensity is sufficient to drive photoreceptor-mediated activity in ganglion cells (not shown), though well below the threshold for hChR2 activation. (B) Blue spots (10 mW/mm$^2$) elicit robust PSD95-hChR2 mediated spiking directly in ganglion cells in the presence of drug cocktail (n=12). (C) Spots of 25, 50, 100, 200, 400, 800, and 1000 µm diameter are flashed for a duration of 500 ms. (D) Spike rate increases as a function of spot diameter (n=12, p value=0.01).

The PSD95-hChR2 fusion was effective at generating spikes in response to patterned blue illumination. Extracellular spike recordings were performed on ganglion cells expressing PSD95-hChR2 during illumination with white or blue spots of increasing diameter while the retina was perfused with synaptic transmission blockers (1-AP4, CPP, CNQX). White spots (0.012 mW/mm$^2$) failed to evoke spike responses regardless of spot diameter (25-1000 μm). This illumination intensity is sufficient to drive photoreceptor-mediated spiking responses in light adapted rabbit retina in the absence of synaptic blockade (not shown), indicating that photoreceptor-mediated synaptic transmission was entirely blocked in the presence of the cocktail (FIG. 3A). In the same cell, blue spots (10 mW/mm$^2$) elicited robust PSD95-hChR2 mediated spikes in response to spots ranging from 25-1000 μm (FIGS. 3B-3D). Spike frequency increased as the spot expanded to illuminate more of the cell's dendritic field.

Example 4

Figure 4:
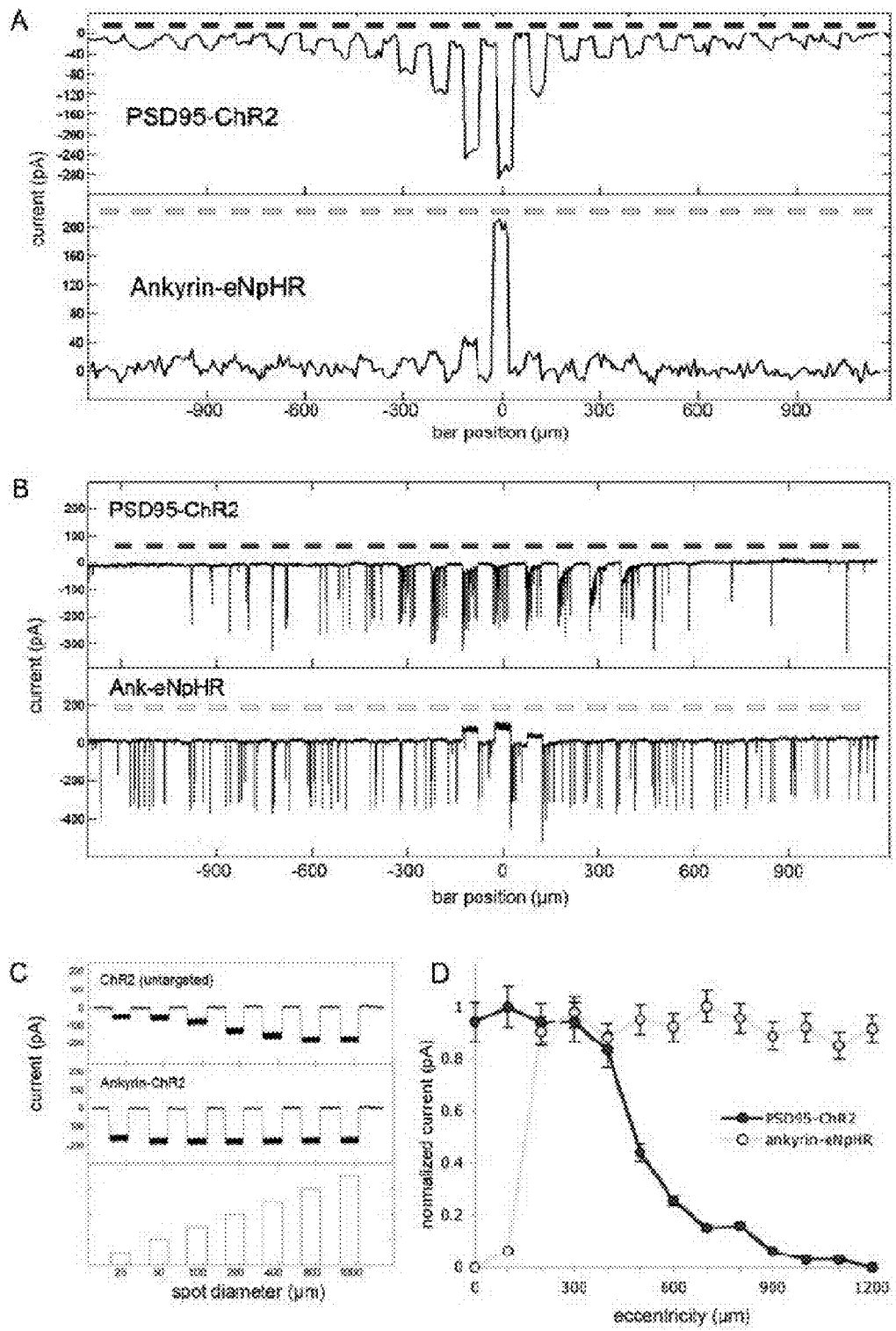
FIG. 4. Response maps of PSD95 and Ankyrin$_G$ targeted opsins show distinct spatial profiles. (A) Representative whole cell voltage clamp recordings (−60 mV) from a ganglion cell simultaneously expressing PSD95-hChR2 and Ankyrin-eNpHR during photo-stimulation with a 100 µm wide dark (top) or light (bottom) bar moved incrementally across the dendritic field. PSD95-hChR2 response map (~600 µm diameter) is significantly larger than Ankyrin-eNpHR response map (~200 µm). Receptive field spread determined by response amplitude threshold of 5% maximum (n=5). (B) Response maps of PSD95-hChR2 and ankyrin$_G$-eNpHR under unclamped spiking conditions. Spikes reveal distinct response areas of hChR2 and eNpHR (n=6). (C) Untargeted hChR2 gives progressively larger inward currents with increasing spot diameters as more of the dendritic field is illuminated while Ankyrin-hChR2 response plateaus at 50 μm spot diameter due to restricted hChR2 localization in the ganglion cell soma. Diameter of the blue spots of 25-1000 μm diameter used to illuminate ganglion cell (n=6). (D) Spikes/second plotted vs. eccentricity from receptive field center. Ankyrin$_G$-eNpHR shows a narrow response profile of <200 um where spikes are suppressed during illumination with 100 um wide bar (light bar). PSD95-hChR2 gives a broad response profile of ~600 um driving robust spiking during blue light illumination (n=5, p value=0.01).

Spatially Differentiated Opsins have Distinct Antagonistic Receptive Field Profiles Excitatory and inhibitory inputs to ganglion cells normally have distinct receptive field profiles. In most cases, the excitatory "center" corresponds roughly to the cell's dendritic field, while the inhibitory "surround" is somewhat larger. In order to recapitulate center-surround antagonism in a ganglion cell lacking synaptic input, we endowed them with excitatory and inhibitory currents generated with opsin transgenes targeted to either the cell body or dendrites. We investigated the spatial pattern of activity generated by these opsins by probing with patterned blue or yellow illumination. Ganglion cells were transfected with a combination of the two opsins consisting of either ankyrin$_G$-eNpHR/PSD95-hChR2 or ankyrin$_G$-hChR2/PSD95-eNpHR. The spatial pattern of expression was confirmed by confocal microscopy (FIGS. 1H-1I) and we investigated the resulting pattern of electrical activity by whole cell voltage clamp holding the membrane at −60 mV while a 100 μm bar was stepped across the dendritic field. To create an OFF-center cell, we expressed a combination of ankyrin$_G$-eNpHR in the soma (inhibitory center) and PSD95-hChR2 in the excitatory surrounding dendrites (FIG. 1I). Electrophysiological recordings confirmed that these two opsins evoke opposing currents with distinct spatial expression profiles (FIG. 4). A stepped blue bar elicited a PSD95-hChR2-mediated inward current response spread of ~600 μm (FIG. 4A). Conversely, ankyrin$_G$-eNpHR mediated an outward current response spread three-fold smaller (~200 μm) on average (FIG. 4A). Under recording conditions that preserve spiking, response fields were also observed to have distinct profiles: PSD95-hChR2 exhibited a significantly broader profile than ankyrin$_G$-eNpHR (FIG. 4B). PSD95-hChR2 effectively drove robust spiking with a broad ~600 μm spread, while ankyrin$_G$-eNpHR suppressed spontaneous spikes with a narrow <200 μm spread (FIG. 4B).

Receptive fields were also mapped by spots of increasing diameter (FIG. 4C). The spatial profile of untargeted-hChR2 was compared to ankyrin$_G$-hChR2 to ensure that activity was targeted to the cell soma. When probed with blue spots of 25-1000 μm diameter, untargeted-hChR2 drove inward currents of progressively greater amplitude as more of the dendritic field was recruited by light (FIG. 4C). However, responses plateaued at 50 μm, indicating that ankyrin$_G$-hChR2 expression was limited to the soma (FIG. 4C). Taken together, these results indicate that the ankyrin$_G$ and PSD-95 motifs successfully chaperone hChR2 and eNpHR differentially to somatic or dendritic compartments, endowing the excitatory and inhibitory currents with distinct spatial profiles (FIG. 4D).

Example 5

Differentially Targeted Opsins Encode Edges and Generate Zero-Crossings

Figure 5:
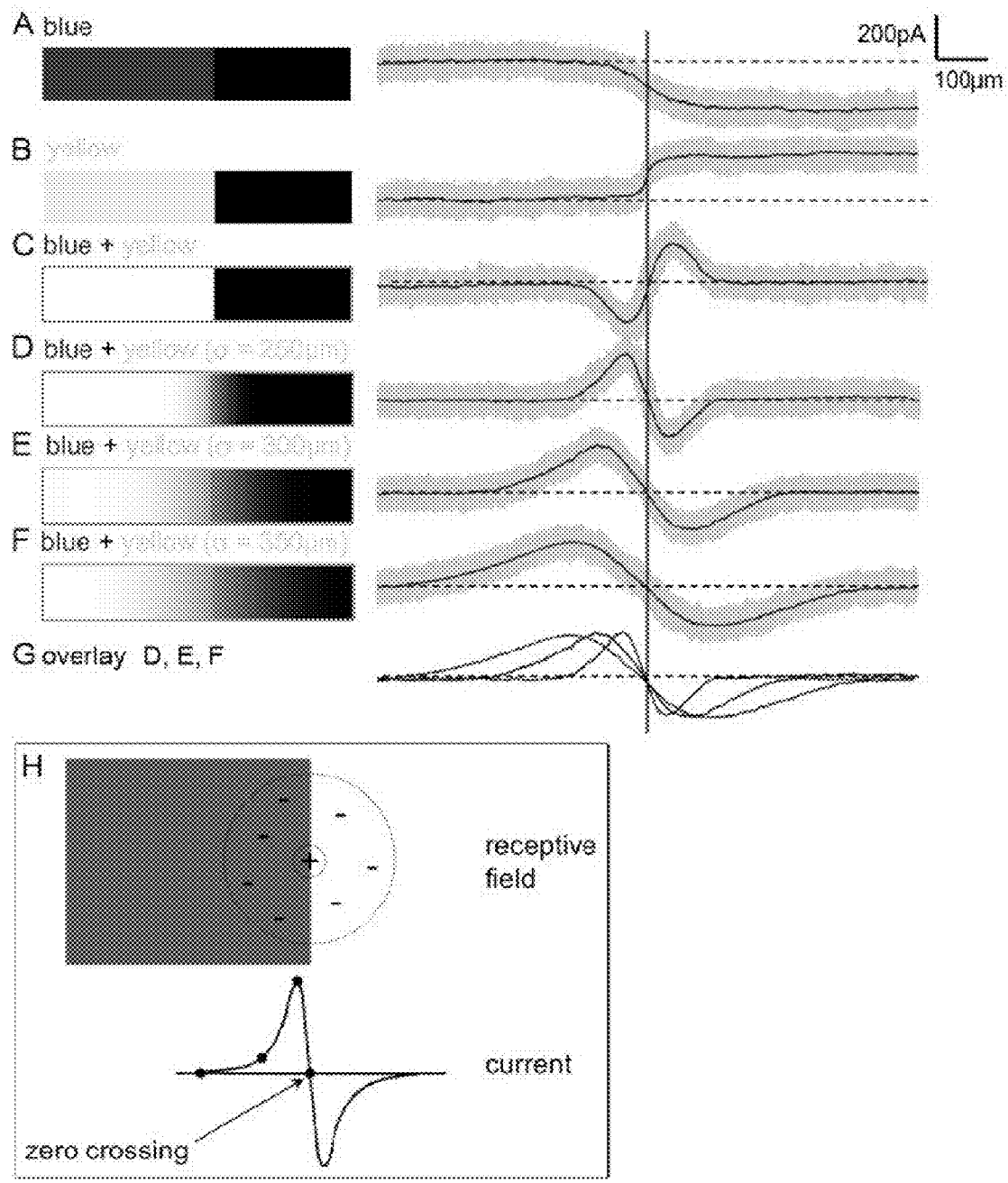
FIG. 5. Edges are properly encoded by simultaneous differential expression of PSD95-hChR2 and Ankyrin-eNpHR. Representative current traces recorded under voltage clamp conditions (−60 mV) in response to movement of an edge from left to right across the dendritic field. Edges in A, B, and C are altered only in their chromatic composition. (A) PSD95-hChR2 mediated inward current in response to dark edge. Edge is encoded as a broad excitatory current with no zero crossing (n=7 cells). Grey shading represents ±standard deviation. (B) Ankyrin-eNpHR mediated outward current response to light edge. Edge is encoded as a sharp inhibitory current, though it still lacks a zero crossing (n=9 cells). (C) Simultaneous activity of differentially targeted PSD95-hChR2 and Ankyrin-eNpHR enables proper encoding of the edge as evidenced by the zero-crossing point due to the presence of center-surround antagonism. Excitation arrives at the cell before inhibition due to the dendritic-hChR2 and somatic-eNpHR localization (n=8 cells). Edges in D, E, and F are modified by convolving only the yellow (light bars) channel with a Gaussian blur kernel of increasing diameter (blue channel or dark bars un-blurred) to manipulate the slope of the mach band at the zero-crossing point. (D) Edge is composed of a Gaussian blurred yellow channel (or light bars) ($\sigma$=250 μm) and un-blurred blue channel (dark bars) enabling the inversion of the mach band such that inhibition arrives at the cell before excitation (n=7 cells). (E) Yellow channel (light bars) is blurred ($\sigma$=300 μm) to decrease the slope of the mach band at the zero crossing point (n=7 cells). (F) Yellow channel (light bars) is blurred even further ($\sigma$=350 μm) resulting in a shallow slope mach band (n=7 cells). (G) Overlay of current traces in D, E, and F. (H) A model edge is encoded properly as evidenced by the presence of a zero crossing point in the simulated current trace. The zero crossing occurs during equal activation of excitatory and inhibitory currents.

How ganglion cells expressing differentially targeted opsins respond to an edge was next investigated. An edge is a particularly useful experimental stimulus because it lacks dimensions and therefore avoids error introduced by stimuli that are poorly aligned with the recorded neuron. Furthermore, if encoded properly by the visual system a true zero-crossing point (Man and Hildreth, 1980) is revealed (FIG. 5H). A series of edges were presented to ganglion cells expressing a combination of ankyrin$_G$-eNpHR and PSD95-hChR2 while currents were recorded in voltage clamp at −60 mV. Edges were modified in both their chromatic and spatial properties to control how a ganglion cell would represent the edge. An hChR2-mediated excitatory inward current grew progressively in amplitude when a blue edge passed across the neuron (left to right), (FIG. 5A). This broad excitatory current mediated solely by PSD95-hChR2 expression failed to generate a zero-crossing because it lacked surround antagonism. A yellow edge evoked a sharp outward inhibitory current mediated by ankyrin$_G$-eNpHR, but still showed no zero-crossing because it also lacked surround antagonism (FIG. 5B). The combination of blue and yellow edges in RGB color space results in a white edge. This white edge initially evokes an inward excitatory current mediated by dendritic-hChR2, followed by a zero-crossing point and an outward inhibitory current mediated by somatic-eNpHR (FIG. 5C). The zero-crossing point was observed when excitation and inhibition were in balance, indicating the edge generated a zero-crossing in this OFF-center cell.

Example 6

Center-Surround Dimensions are not Physiological

Figure 6:
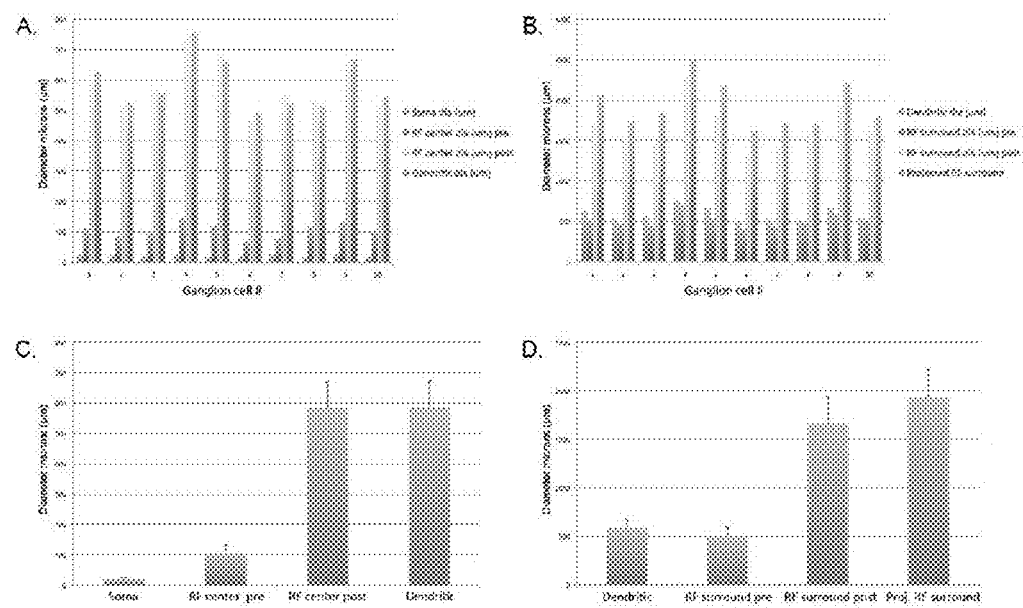
FIG. 6. Transformation of center and surround responses to physiological dimensions. Excitatory center (ankyrin-hChR2) and inhibitory surround (PSD95-eNpHR) response dimensions were mapped for 10 ganglion cells using a marching blue (dark) or yellow (light) bar and restored to physiological dimensions using Gaussian blur. (A) Ankyrin-hChR2 center responses were expanded in 10 ganglion cells using Gaussian blur functions to effectively transform the receptive field center dimension to match the dendritic field diameter. (B) PSD95-eNpHR surround responses were expanded to transform the receptive field surround dimension to match the projected surround dimension with a center-surround ratio of 1:3.28. (C) Average and standard deviation of center response diameter is expanded from 106±26 μm to 582±87 μm using Gaussian blur. (D) Surround response diameter is expanded from 504±85 μm to 1663±280 μm, approximately equivalent to the projected surround diameter fitting the center-surround ratio of 1:3.28. For a set of four bars for each cell in panel A, from left to right: soma diameter, RF center diameter pre, RF center diameter post, dendritic diameter. For each set of four bars in panel B, from left to right: dendritic diameter, RF surround diameter pre, RF surround post, projected RF surround.

Genetic targeting of opsins to the soma and dendrites using the ankyrin$_G$ and PSD-95 motifs results in non-physiological center-surround dimensions. Ganglion cells normally have receptive field centers slightly smaller than the dendritic field and surrounds that are three to five times larger than the center. But our genetically engineered ganglion cells demonstrate centers slightly larger than the soma and surrounds roughly equivalent to the dendritic field diameter. These responses were able to be transformed to restore more physiological receptive field dimensions by manipulating the spatial profiles of the two stimuli using distinct wavelengths corresponding to the action spectrum of each opsin. For example, the response profile of the cell body was convolved with a yellow input image Gaussian filter with dimensions corresponding to the physiological receptive field surround, while leaving the blue channel unaltered (FIG. 5D-5G). In this series, the yellow channel was blurred with a Gaussian filter ($\sigma$=250-350 µm) to reveal the modified representation of the edge. With this blur, the inhibitory receptive field dimension increased such that the outward current preceded the inward current, inverting the edge representation (FIG. 5D). As the yellow channel was progressively more blurred, the slope of the resultant edge response at the zero-crossing point decreased (FIG. 5D-5G). Thus, by independently Gaussian blurring the input image for one or both of the opsins, the surround activity increased to dimensions beyond those that are spatially defined by the opsin expression profile. The receptive field diameters of both excitatory center and inhibitory surround domains can be modulated with Gaussian blurring of the two distinct illumination colors (blue vs. yellow). This is demonstrated using a marching bar stimulus where the excitatory center (ankyrin-hChR2) is expanded six-fold on average from ~100 µm to ~600 µm to restore physiological center response dimensions (FIG. 6). Using this technique, the excitatory center of ten ganglion cells was successfully restored to physiologically relevant diameters approximately equivalent to the dendritic field diameter of each cell (FIG. 6A, 6C). Similarly, the receptive field surround dimensions of these ten cells were also restored to physiologically relevant diameters (FIG. 6B, 6D) approximately 3.3 fold larger than the center, a spatial area much greater than the dendritic expression of the opsin (Lee et al. (1998) *Vis Neurosci* 15:161-175). This system, comprised of genetic targeting of the antagonistic opsins along with image preprocessing with Gaussians, enables independent control of the spatial dimensions of excitation and inhibition, reestablishing physiological receptive field dimensions. Furthermore, we could dynamically change the cell's membrane potential by adjusting the relative intensity of the two input wavelengths.

Disucssion

Figure 7:
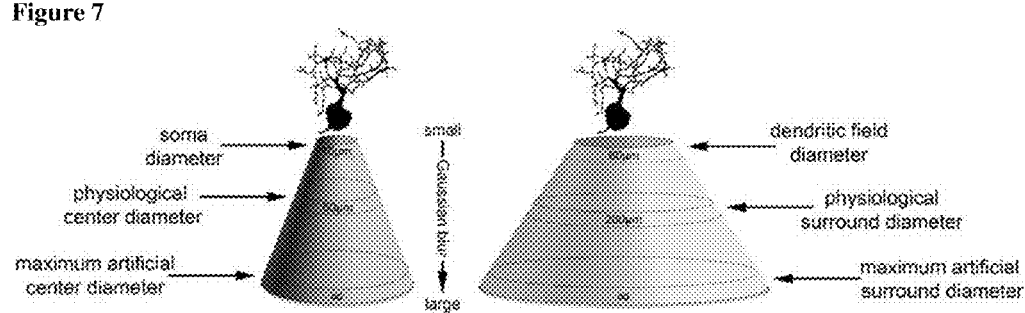
FIG. 7. Adjustment of center and surround receptive field diameters by introducing a Gaussian blur. A midget cell receptive field center is depicted in dark gray (blue), the surround in light gray (yellow). The receptive field of the center channel is expanded from the 10 μm soma out to the 60 μm physiological center with increasing Gaussian blur. Similarly, the receptive field surround is expanded from the 60 μm dendritic field out to the 200 μm physiological surround.

Targeting the photosensitive neuromodulators hChR2 and eNpHR to distinct subcellular compartments can endow ganglion cells with differential spatial and spectral photosensitivity generating center-surround antagonistic receptive fields. The two opsins were chaperoned to either the ganglion cell soma/proximal dendrites by ankyrin$_G$ or the dendritic tree by PSD-95 fusion. Excitatory and inhibitory currents were independently activated with either blue or yellow illumination, and the spatial dimensions of the re-created receptive fields were modulated by introducing the appropriate Gaussian blur to the input image (FIG. 7)

Image Preprocessing of Excitatory and Inhibitory Inputs. Based on the behavior of these antagonistic opsins in isolated rabbit retinal explants, we sought to simulate human retinal function when subjected to a similar manipulation. Images were preprocessed and presented to an array of simulated human midget ganglion cells spanning the central 30×22.5° (9×6.75 mm) of visual field. Midget cells are the most prevalent ganglion cell type within 8 mm eccentricity of the primate fovea. They represent 95% of all ganglion cells within 4 mm and 70% from 4-8 mm eccentricity (Dacey (1993) *J Neurosci* 13:5334-5355). Therefore, the simulation was based on midget ganglion cells in the central 30° and selected those with an average soma diameter of 10 µm and dendritic field of 60 µm (Dacey (1993) *J Neurosci* 13:5334-5355). Primate midget cells are reported to have a center-surround size ratio of 1:3.28 (Lee et al. (1998) *Vis Neurosci* 15:161-175). The amplitude of receptive field surround of these cells is reported to be 80% of that of the center (Lee et al. (1998) *Vis Neurosci* 15:161-175). Based on these physiological parameters, we modeled the human midget ganglion cell output to differentially expressed somatic-eNpHR and dendritic-hChR2.

Figure 8:
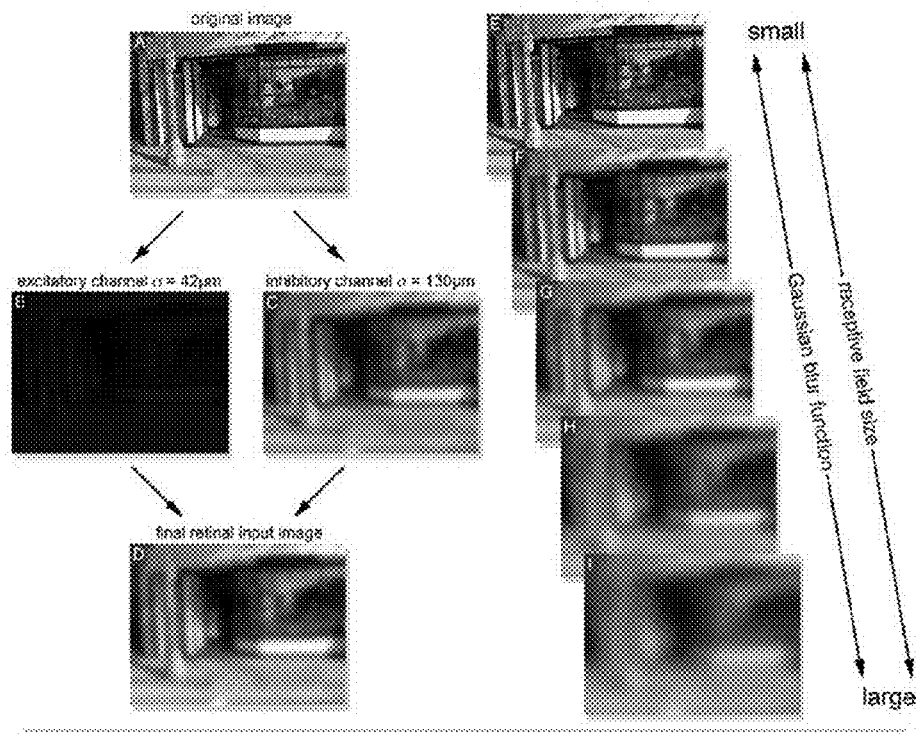
FIG. 8. Retinal input image preprocessing and simulated retinal output or primate parafoveal midget ganglion cells. (A) Original image (640×480 pixels) is split into two channels, one excitatory (dark or blue) and one inhibitory (light or yellow). (B) Excitatory center channel is converted to a bluescale image to stimulate PSD95-hChR2 and convolved with a Gaussian blur filter of 3 pixels FWHM ($\sigma$=42 μm) to avoid aliasing that would occur if spatial information above the Nyquist frequency is presented to midget ganglion cells with a 60 μm dendritic field diameter. Nyquist limit for primate midget ganglion cells=$1/(\sqrt{3}\times$ dendritic field diameter). (C) Inhibitory surround channel is converted to a yellowscale (light gray) image to stimulate Ankyrin-eNpHR and convolved with a 9.3 pixel ($\sigma$=130 μm) Gaussian blur filter to expand the receptive field size of the 10 μm diameter midget cell soma out to a physiologically relevant 200 μm. (D) Final input image to the retina is the sum of images B and C. (E-I) Relationship between blur and receptive field size is illustrated as the blur function is increased from 0, 70, 140, 211, 281 μm Gaussian blur. (J) Gaussian blur function ($\sigma$=57 μm) simulates the excitatory center retinal output from PSD95-hChR2 expressing midget cells with a 60 μm dendritic field diameter. The natural scene is largely preserved with some mid blur. This function ($\sigma$=57 μm) is composed of two gaussians representing the Nyquist sampling frequency ($\sigma$=60 μm) and the receptive field center diameter ($\sigma$=42). (K) Inhibitory surround represented by the Gaussian blur function ($\sigma$=130 μm) greatly blurs the scene. (L) Difference of center and surround Gaussians functions J and K with a physiological center-surround weighting of 5:4 gives maximal edge extraction of the scene. (M) Addition of a filter representing the hexagonal sampling matrix of 60 μm dendritic field diameter cells. Scene features and edge extraction is preserved despite the down sampling provided by the hexagonal matrix. (N-R) The effect of various center-surround ratios is demonstrated ranging from 5:1 to 1:5. A ratio of 5:4 extracts edges most effectively in P.
Figure 8:
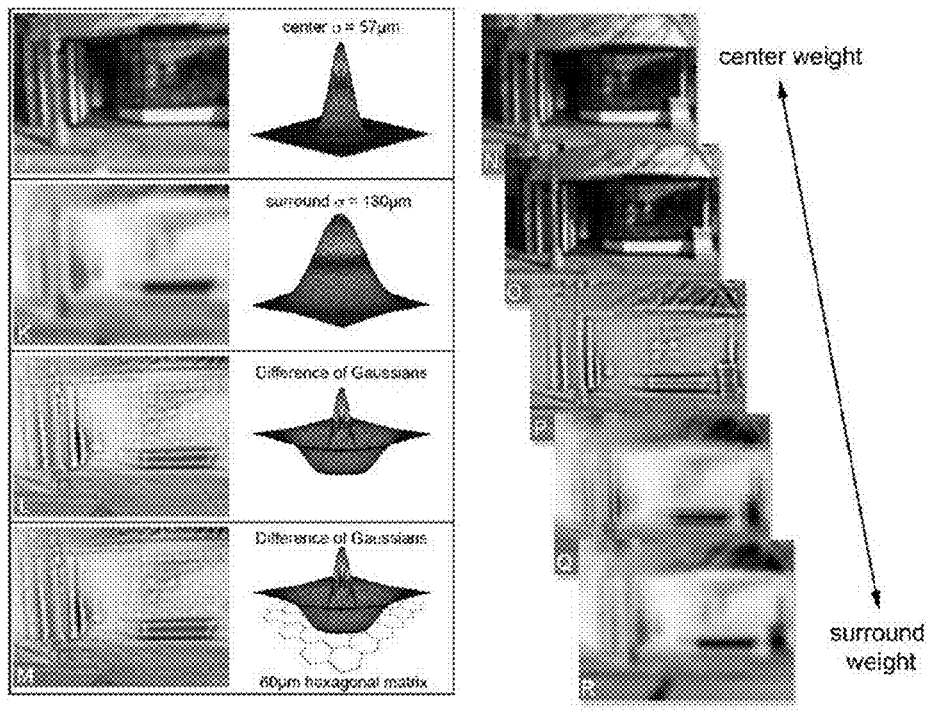
Figure 9:
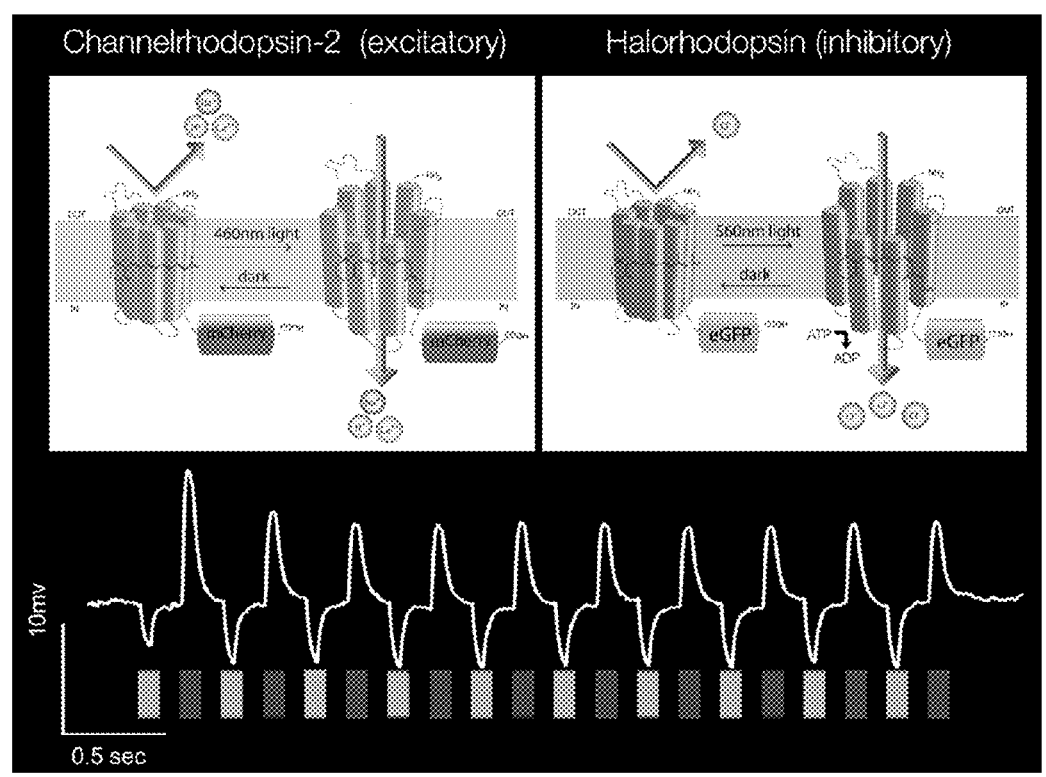
FIG. 9. Channelrhodpsin-2 is a nonspecific cation channel sensitive to blue light (dark bars) (460 nm) that drives excitatory depolarizations in neurons. Halorhodopsin is a chloride pump sensitive to yellow light (light bars) (560 nm) that drives inhibitory hyperpolarizations in neurons.
Figure 10:
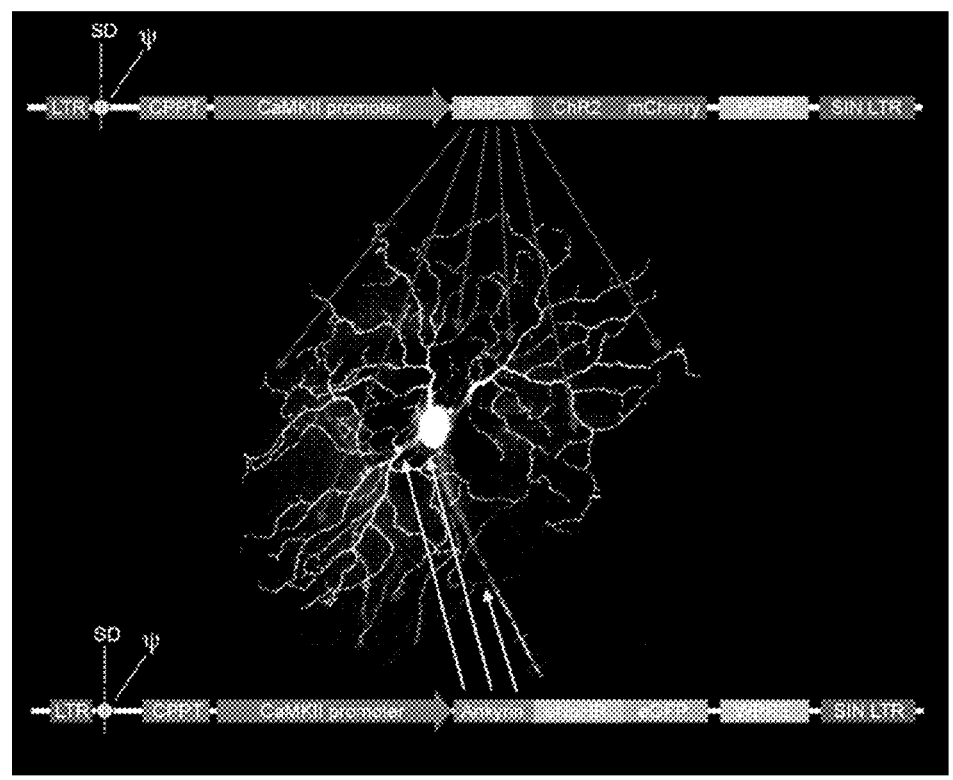
FIG. 10. Constructs engineered to differentially target channelrhodopsin-2 (ChR2) and halorhodopsin (eNpHR) to discrete subcellular domains. A fusion protein consisting of PSD-95-ChR2-mCherry is used to drive excitation in the dendrites (top). A second fusion protein of AnkyrinG-eNpHR-eGFP is used to drive inhibition in the soma of the neuron.
Figure 11:
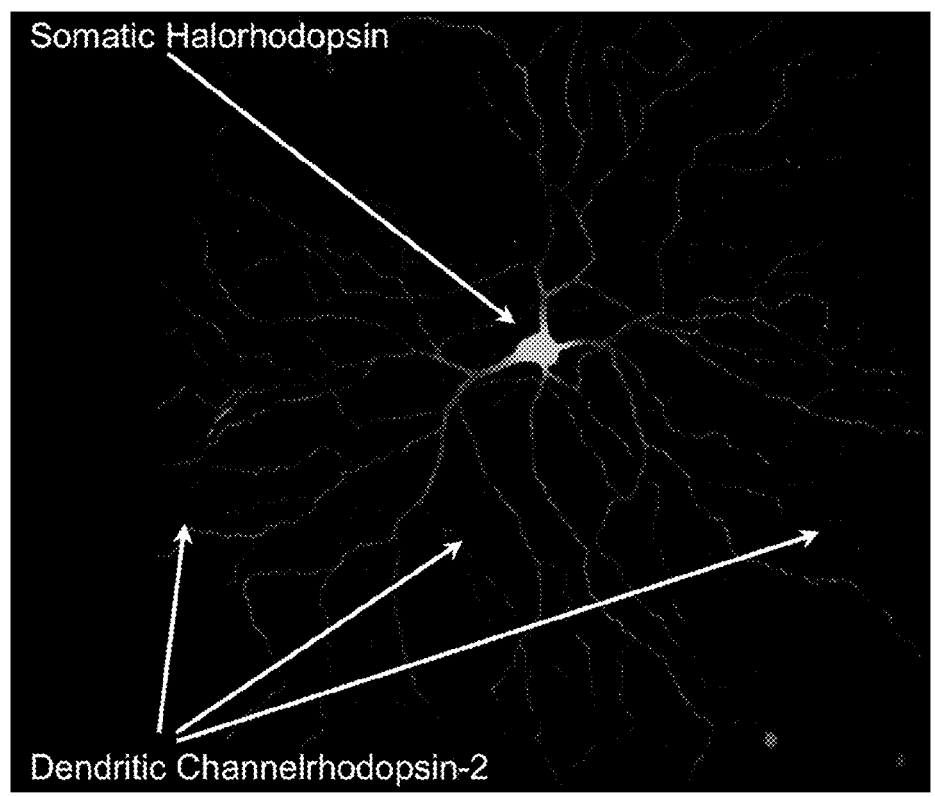
FIG. 11. Halorhodopsin-GFP (inhibitory) is targeted to the soma by the Ankyrin-G targeting motif (green). Channelrhodopsin-2 (excitatory) is targeted to the dendrites by the PSD95 motif (red). Differential targeting of these two antagonistic opsins endows this neuron with center-surround antagonism to behave as an OFF-center ganglion cell.

FIG. 8 shows how a natural scene is preprocessed in order to recreate physiological midget ganglion cell receptive field dimensions. The original grayscale image (640×480 pixels) of a natural scene was preprocessed into two channels, one blue (dark) and one yellow (light) (FIG. 8A-C). The excitatory blue channel was then convolved with a Gaussian blur function ($\sigma$=42 µm) to avoid aliasing that would result if information of higher spatial frequency than the Nyquist frequency were presented to the cell (FIG. 8B). The inhibitory yellow channel was convolved with a significantly larger Gaussian function ($\sigma$=130 µm) to effectively expand the surround receptive field diameter from the 10 µm soma out to 200 µm, based on the physiological center-surround dimensions of 1:3.28 (FIG. 8C). The two modified channels were then overlaid to form a composite image representing the final retinal input (FIG. 8D). Individual blue and yellow components of each channel are prominent in edges of this input image due to the Gaussian blur functions unique to each channel. Here blur was used both to avoid aliasing in the excitatory channel and to increase the receptive field area of the inhibitory channel. Receptive field size increases as a function of the degree of blur as the $\sigma$ value of the Gaussian function is progressively increased from $\sigma$=0-281 µm (FIG. 8E-I). Although feature resolution is lost with increased blur, spatial information is integrated over a larger area allowing for increased receptive field size.

Simulated Output of Parafoveal Primate Midget Ganglion Cells. Using the preprocessing functions described above as the retinal input image, the retinal output of parafoveal primate midget ganglion cells expressing ankyrin$_G$-eNpHR and PSD95-hChR2 was simulated. The simulation represents the output of an array of 17,000 midget cells located within the central 30° field with an average 10 µm diameter soma, 60 μm diameter dendritic field, center-surround area ratio of 1:3.28, and center-surround amplitude of 5:4. The original excitatory input image (FIG. 8B) was convolved with a second Gaussian filter (σ=39 μm) to represent the excitatory center receptive field of a midget cell. The two Gaussian filters were combined (square root of the sum of squares) to give an excitatory hChR2 mediated center output represented by the Gaussian function σ=57 μm (FIG. 8J, supplemental Movie 1). The surround output is represented by grayscale inversion for inhibition and the Gaussian blur function σ=130 μm (FIG. 8K, supplemental Movie 1). The difference of Gaussians is generated by subtracting the above center and surround functions (FIG. 7A-7B) to generate the difference image (FIG. 8L, supplemental Movie 1) using the formula:

$$G(x, y) = \frac{1}{\sigma_{cen}\sqrt{2\pi}} e^{-(X^2+Y^2)/2\sigma_{cen}^2} - \frac{1}{\sigma_{sur}\sqrt{2\pi}} e^{-(X^2+Y^2)/2\sigma_{sur}^2}$$

Where $\sigma_{cen}$ is G the standard deviation of the Gaussian representing the receptive field center, and σsur representing the surround. The center-surround weighting of 5:4 used here is derived from direct measurements from primate midget ganglion cells and nicely extracts edges from the scene. In the final layer of the retinal output, the difference image (FIG. 8L) is down-sampled through a hexagonal matrix to represent discrete sampling of an array of ~17,000 midget cells with a 60 μm dendritic field diameter (FIG. 8J). Even at this down-sampling level, features are retained to a high degree suggesting that midget ganglion cells will encode spatial vision accurately. Furthermore, edges are extracted effectively under these conditions, indicating that physiologically relevant edge detection could be performed via targeted delivery of hChR2 and eNpHR to midget cells. Because each opsin responds to distinct illumination wavelengths, this system allows for dynamic tuning of center-surround ratios by preprocessing the input image appropriately. Examples of multiple retinal output images demonstrate the effect of tuning with center-surround ratios from 5:1 to 1:5 (FIGS. 8N-R). Edge extraction is maximally obtained with the physiological center-surround ratio of 5:4 (FIG. 8P).

Proper Edge Encoding is Necessary For Vision. Differential expression and stimulation of antagonistic opsins enabled ganglion cells to encode edges properly as shown by the presence of a zero-crossing point. However, ganglion cells behave as simple luminance detectors with no zero-crossing point when either opsin is stimulated independently, indicating that hChR2 expression alone in ganglion cells will not likely enable useful spatial vision. It was proposed that different scales of zero-crossings are combined by the visual system to encode major image boundaries. Difference of Gaussian (DoG) convolutions derived from midget ganglion cell physiological parameters demonstrated that optimal edge extraction is attainable with this system. Processes analogous to DoG convolutions operate in the early stages of mammalian vision and center-surround antagonism is present from the retina to the visual cortex. These operations are likely an efficient way to encode visual scenes since retinal mechanisms have evolved to transmit edge and contrast information along the optic nerve.

Combination Optical Neuromodulator-Based Prosthetics. All optical neuromodulator-based retinal prosthetics will likely require some degree of image preprocessing which could be achieved by custom fabricated lightweight micro-LED based head mountable goggles (Degenaar et al. (2009) *J Neural Eng* 6:035007). When expressed in retinal bipolar or ganglion cells, the current generation of hChR2 requires significantly more light (5 log units) for activation than mammalian photoreceptors (hChR2=$10^{15}$ photons cm$^{-2}$ s$^{-1}$, cones=$10^{10}$ photons cm$^{-2}$ s$^{-1}$, and rod=$10^{6}$ photons cm$^{-2}$ s$^{-1}$). Fortunately, the current generation of high intensity micro-LED arrays can satisfy these intensity requirements, delivering up to 100 mW cm$^{-2}$, though illumination levels must be kept to a minimum to prevent phototoxicity to the retina. The development of more sensitive neuromodulators and molecular signal amplification mechanisms is currently underway to circumvent this issue.

Another hurdle facing hChR2 based prosthetics is their limited dynamic range when compared to normal photoreceptors. The normal retina responds to changes in illumination levels of 10 log units when transitioning from starlight to sunlight, however hChR2 responses are limited to 2 log units. Cone photoreceptors adapt so that our visual system can detect visual features ranging from dim shadows to objects in bright sunlit snow, a range spanning 7-9 log units of light intensity. To avoid saturation and most effectively use the 2 log dynamic range of hChR2 and eNpHR, input illumination hardware will require signal compression and a local gain control mechanism. Fortunately, high-end CCD cameras currently available have the ability to perform local gain control and dynamic range compression.

The overall system that we describe will utilize an additional component of preprocessing to adjust effective receptive field dimensions introduced via channel separation and Gaussian blur. By combining antagonistic targeting with Gaussian blur convolution of each channel independently (blue (dark) vs. yellow (light)), ganglion cells will be able to encode edges even though they will receive no synaptic input. Membrane potential level can be adjusted by setting the relative intensities of the antagonistic stimuli. This system will allow complete control of intensity, dynamic range, receptive field dimensions and membrane potential level.

Inner Retinal Remodeling During Degeneration. During the course of retinal degeneration in the rd1 mouse, early-onset anatomical changes in rod and cone bipolar cells occur as their dendrites retract and axon terminals atrophy, resulting in morphologically immature synapses. The molecular signature of bipolar cells also undergoes changes as ON bipolar cells downregulate mGluR6, and upregulate AMPA/Kainate receptors, switching their identity from ON to OFF. These alterations in bipolar cells indicate that inner retinal integrity must be carefully considered before visual restoration is attempted at the photoreceptor or bipolar cell level. Lagali et al. recently demonstrated that ON bipolar cells expressing hChR2 can convey information to ON ganglion cells in the rd1 retina. Interestingly, rod bipolar cells failed to activate light responses in OFF ganglion cells as would be expected through the AII amacrine cell pathway. This lack of OFF responses in ganglion cells may indicate that the rod bipolar-AII-OFF ganglion cell pathway is compromised in the rd1 mouse. Although bipolar cells undergo significant morphological and molecular changes during retinal degeneration, ganglion cell morphology and projections remain surprisingly well preserved despite the lack of photoreceptor input (Mazzoni (2008) *J Neurosci* 28:14282-14292). Ganglion cells apparently maintain their characteristic ON and OFF dendritic stratification, intrinsic firing properties, rebound firing, balance of synaptic excitation and inhibition, and dendritic calcium signaling even into late stages of degeneration.

Modulating Ganglion Cell Activity in Diseased Retinas. Despite observations that ganglion cells survive and maintain normal dendritic morphology long after rods and cones are lost, they exhibit sustained and spontaneous hyperactivity in rd1 retinas. This hyperactivity may be the result of strong rhythmic synaptic input to both ON and OFF ganglion cells. The system that we describe enables the basal "spontaneous" spiking level to be dynamically modulated. In this system, eNpHR inhibition could silence degeneration-induced visual artifacts, and would enable excitatory hChR2 activity to most efficiently utilize the relatively narrow 2.5 log unit dynamic range of the ganglion cell spike generator. For a therapeutic approach to be most effective, the subject method can restrict expression to a specific subclass of ganglion cell. Some recent studies have correlated gene expression profiles with physiologically discrete classes of ganglion cells, which could provide insights to transcriptionally target these opsins appropriately in a diseased retina (Greenberg (2007) *Invest Ophthalmo Vis Sci* 48:E-abstract 1977; Huberman (2009) *Neuron* 62:327-334).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of inducing photosensitivity and ability to detect edge in a neuronal cell, wherein said neuronal cell is a retinal ganglion cell, comprising:
introducing channelrhodopsin-2 and halorhodopsin into said neuronal cell by targeting channelrhodopsin-2 and halorhodopsin to subcellular regions of said neuronal cell;
wherein said channelrhodopsin-2 is fused to a first targeting element that targets expression of said channelrhodopsin-2 in soma of said neuronal cell, wherein the first targeting element is ankyrin$_G$, wherein said halorhodopsin is fused to a second targeting element that targets expression of said halorhodopsin in dendrites of said neuronal cell, wherein the second targeting element is PSD-95, thereby creating an ON-center neuronal cell comprising center-surround antagonism, or wherein said channelrhodopsin-2 is fused to a first targeting element that targets expression of said channelrhodopsin-2 in dendrites of said neuronal cell, wherein the first targeting element is PSD-95, wherein said halorhodopsin is fused to a second targeting element that targets expression of said halorhodopsin in soma of said neuronal cell, wherein the second targeting element is ankyrin$_G$, thereby creating an OFF-center neuronal cell comprising center-surround antagonism.

2. The method according to claim 1, wherein said neuronal cell is in a degenerate retina.

3. The method according to claim 2, wherein said degenerate retina has decreased number of photoreceptors relative to a healthy retina.

4. The method according to claim 1, wherein said neuronal cell is a mammalian retinal ganglion cell.

5. The method according to claim 4, wherein said neuronal cell is a human retinal ganglion cell.

6. The method according to claim 4, wherein said neuronal cell is in a human patient.

7. The method according to claim 1, wherein the first targeting element that targets expression of said channelrhodopsin-2 in soma of said neuronal cell is ankyrin$_G$ and the second targeting element that targets expression of said halorhodopsin in dendrites of said neuronal cell is PSD-95.

8. The method according to claim 1, wherein the first targeting element that targets expression of said channelrhodopsin-2 in dendrites of said neuronal cell is PSD-95 and the second targeting element that targets expression of said halorhodopsin in soma of said neuronal cell is ankyrin$_G$.

* * * * *